US008440801B2

(12) United States Patent
Nakamura et al.

(10) Patent No.: US 8,440,801 B2
(45) Date of Patent: May 14, 2013

(54) APTAMER AGAINST IL-17 AND USE THEREOF

(75) Inventors: Yoshikazu Nakamura, Tokyo (JP); Shoji Ohuchi, Tokyo (JP); Akira Ishiguro, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 13/003,240

(22) PCT Filed: Jul. 14, 2009

(86) PCT No.: PCT/JP2009/062764
§ 371 (c)(1),
(2), (4) Date: Mar. 24, 2011

(87) PCT Pub. No.: WO2010/008001
PCT Pub. Date: Jan. 21, 2010

(65) Prior Publication Data
US 2011/0177578 A1    Jul. 21, 2011

(30) Foreign Application Priority Data

Jul. 14, 2008   (JP) ................................. 2008-183233

(51) Int. Cl.
*C07H 21/02* (2006.01)
*C12Q 1/68* (2006.01)
*A61K 48/00* (2006.01)

(52) U.S. Cl.
USPC ........................... 536/23.1; 435/6.1; 514/44 R

(58) Field of Classification Search .................. None
See application file for complete search history.

(56) References Cited

U.S. PATENT DOCUMENTS

2004/0137010 A1    7/2004  Wilson et al.
2005/0260651 A1 *  11/2005  Calias et al. ..................... 435/6
2006/0193821 A1    8/2006  Diener et al.
2009/0170219 A1    7/2009  Nakamura et al.
2010/0256038 A1 *  10/2010  Curnock .................... 514/1.1

FOREIGN PATENT DOCUMENTS

| CA | 2 596 509 A1 | 8/2006 |
| EP | 1938802 A1 | 7/2008 |
| JP | 2006-506055 A | 2/2006 |
| JP | 2007-527246 A | 9/2007 |
| WO | 2006/088925 A2 | 8/2006 |
| WO | WO 2007/004748 A | 1/2007 |
| WO | WO 2007/035922 A | 3/2007 |
| WO | WO 2008/028081 A2 | 3/2008 |

OTHER PUBLICATIONS

Lanfranchi et al (Genome Res. 6 (1), 35-42 (1996)).*
Canadian Patent Office, Office Action in Canadian Patent Application No. 2,730,796 (Jul. 23, 2012).
Adachi et al., *Biochimie*, 93: 1081-1088 (2011).
Chen et al., *Osteoarthritis and Cartilage*, 19(6) 711-718 (2011).
European Patent Office, Supplementary European Search Report issued in European Patent Application No. 09 79 7926 (Dec. 11, 2012).
Ishiguro et al., *Arthritis and Rheumatism*, 63(2): 455-466 (2011).
Nakamura et al., *Genes to Cells*, 17: 344-364 (2012).
Zhou et al., *Cytokine*, 38(3): 157-164 (2007).

* cited by examiner

*Primary Examiner* — Richard Schnizer
(74) *Attorney, Agent, or Firm* — Leydig, Voit & Mayer, Ltd.

(57) ABSTRACT

The invention provides an aptamer possessing an inhibitory activity against IL-17, as well as a complex comprising an aptamer possessing a binding activity or inhibitory activity against IL-17 and a functional substance (for example, affinity substances, substances for labeling, enzymes, drug delivery vehicles, drugs and the like). The invention also provides a pharmaceutical drug, cell migration inhibitor, diagnostic reagent, detection probe, carrier, labeling agent, and the like comprising the aforementioned aptamer or complex, and methods of detecting and purifying IL-17 by using the aforementioned aptamer or complex.

13 Claims, 11 Drawing Sheets

US 8,440,801 B2

APTAMER AGAINST IL-17 AND USE THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,556 bytes ASCII (Text) file named "707478Replacement-SequenceListing.txt," created Dec. 17, 2012.

TECHNICAL FIELD

The present invention relates to an aptamer against IL-17, a method of utilizing the same, and the like.

BACKGROUND ART

Interleukin 17 (IL-17 or CTLA-8), a cytokine secreted by Th17 cells, is profoundly associated with inflammatory diseases, autoimmune diseases, and infectious diseases. Human IL-17 is a 20-30 kDa glycoprotein configured with 155 amino acids, comprising a signal peptide at the N-end. In the molecular structure thereof, six cysteine residues and one N-binding sugar chain binding site are present. The mature form consists of 136 amino acids, normally occurring as a dimer.

As proteins of the IL-17 family, six kinds of proteins are known: IL-17A, B, C, D, E, and F. Generally, IL-17 refers to IL-17A. IL-17E is also called IL-25. The amino acid sequence homology of human IL-17 to human IL-17B, C, D, E, and F is 25, 28, 22, 27, and 44%, respectively, IL-17F being of the highest homology. Human IL-17 has homologies of 63% and 90% to mouse IL-17 and marmoset IL-17. As receptors thereof, IL-17RA, IL-17RB, IL-17RC, IL-17RD, and IL-17RE are known. IL-17 and IL-17F form a homodimer or heterodimer and binds to IL-17RA and IL-17RC. The binding of IL-17 and IL-17RA is weak at a Kd value of about $10^{-7}$, suggesting that the involvement of IL-17RC may be important.

The Th17 cells are CD4$^+$ T cells that produce IL-17. When memory CD4$^+$. T cells are stimulated with IL-23 in vitro, IL-17 production is induced. Meanwhile, TGF-β and IL-6 play an important role in the differentiation induction of Th17 cells. TGF-β and IL-6 act on naive T cells to induce the expression of RORgt (transcriptional factor). Because a deficiency in RORgt makes Th17 cells to be unable to differentiate, and also because naive T cells can conversely be differentiated into IL-17-producing cells by forcibly expressing RORgt, this transcriptional factor is thought to be important to the differentiation of Th17 cells. Although activation of STAT3 by IL-6 is important to the induction of the expression of RORgt, activation of STAT5 by IL-2 conversely suppresses the expression. IL-2 is necessary for the differentiation of regulatory T cells; IL-2-deficient mice experience serious autoimmunity; this is thought to be due to a decrease in regulatory T cells and concurrent over-differentiation of Th17 cells. When naive T cells are stimulated with TGF-β alone in vitro, not Th17, but regulatory T cells, are induced. IFN-γ produced by Th1 cells, IL-4 produced by Th2 cells, and the like work suppressively on the differentiation of Th17 cells.

When IL-17 binds to a receptor, the NF-κB pathway, MAP kinase pathway, and C/EBP pathway are activated via Act-1 and TRAF6, resulting in the induction of inflammatory cytokines and chemokines. For example, IL-17 acts on macrophages to induce the expression of IL-1, TNF, MMP-9 and the like. In addition, IL-17 is known to act also on connective tissue system cells such as fibroblasts and endothelial cells, and on immune system cells such as dendritic cell progenitor cells, to induce the expression of various cytokines and receptors such as IL-6, IL-1, and ICAM-1.

Involved in the production of IL-17 are cytokines such as TNF-α, IL-1β, IL-6, and IFN-γ. Meanwhile, production of these cytokines is induced by IL-17. IL-17 is known to act synergistically with other cytokines.

IL-17 has been found to be profoundly associated with inflammatory diseases, autoimmune diseases and the like. It is known that the expression of IL-17 is elevated in patients with chronic rheumatoid arthritis, systemic lupus erythematosus, Behçet's disease, graft rejection, nephritic syndrome, inflammatory bowel disease, asthma, multiple sclerosis, periodontal disease and the like. In IL-17-deficient mice, it has been reported that collagen-induced arthritis (CIA), which is a model of chronic rheumatoid arthritis; experimental autoimmune encephalomyelitis (EAE), which is a model of multiple sclerosis; contact type hypersensitivity reactions by DNFB or TNCB; delayed type hypersensitivity reactions by methylated BSA; airway hypersensitive reactions by OVA induction, and the like are remarkably suppressed.

IL-17 is also associated with cancers. It has been reported that subcutaneous transplantation of non-small cell lung cancer cells to SCID mice promotes the proliferation of cancer cells in mice having IL-17 expressed highly therein. It has also been reported that IL-17 is also associated with uterine cervical cancer and ovarian cancer.

IL-17 is associated with infectious diseases. IL-17R-knockout mice are highly susceptible to *Klebsiella pneumoniae* infection, *Candida albicans* infection, *Toxsoplasma gondii* infection and the like. IL-17 production is induced by lipopolysaccharides (LPS) and bacterial cell body components such as of *Borrelia burgdorferi* and *Klebsiella pneumoniae*. These components are thought to promote IL-17 production by acting on antigen-presenting cells to induce IL-23. In IL-17R-knockout mice, after *Klebsiella pneumoniae* infection, in infected sites in the lung, the production of CXCL1, CXCL2, G-CSF and the like, which play an important role in the migration and functions of neutrophils, has been reduced, with a disturbance noted in the migration of neutrophils.

In recent years, applications of RNA aptamers to therapeutic drugs, diagnostic reagents, and test reagents have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target molecule such as a protein, and can be prepared using the SELEX (Systematic Evolution of Ligands by Exponential Enrichment) method (International Patent Publication WO91/19813, WO94/08050, WO95/07364). In the SELEX method, an RNA that binds specifically to a target molecule is selected from an RNA pool with about $10^{14}$ different nucleotide sequences. The RNA used has a random sequence of about 40 residues, which is flanked by primer sequences. This RNA pool is allowed to mix with a target molecule, and only the RNA that has bound to the target molecule is collected using a filter and the like. The RNA collected is amplified by RT-PCR, and this is used as a template for the next round. By repeating this operation about 10 times, an RNA aptamer that binds specifically to the target molecule can be acquired.

PRIOR ART DOCUMENTS

Patent Documents patent document 1: WO91/19813
patent document 2: WO94/08050
patent document 3: WO95/07364

SUMMARY OF THE INVENTION

Problems to be Solved by the Invention

The present invention is directed to providing an aptamer for IL-17 and a method for utilizing the same, and the like.

Means of Solving the Problems

The present inventors investigated diligently to solve the problem described above and succeeded in preparing an aptamer of good quality for IL-17, which resulted in the completion of the present invention.

Accordingly, the present invention provides the following:

[1] an aptamer that binds to IL-17;
[2] an aptamer that inhibits the binding of IL-17 and IL-17 receptor;
[3] an aptamer that inhibits the binding of IL-17 and IL-17 receptor but does not inhibit the binding of IL-17F and IL-17 receptor;
[4] an aptamer that inhibits the binding of IL-17 and IL-17 receptor, and that comprises the sequence of SEQ ID NO:58;
[5] an aptamer that inhibits the binding of IL-17 and IL-17 receptor, and that comprises the sequence of SEQ ID NO:59 or 60;
[6] the aptamer described in [4] or [5], wherein the pyrimidine nucleotide is a modified nucleotide;
[7] the aptamer of [1], which is either (a) or (b) below:
(a) an aptamer comprising a nucleotide sequence selected from among SEQ ID NO:1 to 54 (with the provision that the uracil may be thymine), wherein the nucleotides contained in the aptamer are such that,
    (i) each 2'-position of ribose of the pyrimidine nucleotide is the same or different and is a fluorine atom or substituted by atom or group selected from the group consisting of hydrogen atom, hydroxy group and methoxy group, and
    (ii) each 2'-position of ribose of the purine nucleotide is the same or different and is hydroxy group or substituted by atom or group selected from the group consisting of hydrogen atom, methoxy group and fluorine atom;
(b) an aptamer comprising a nucleotide sequence selected from among SEQ ID NO:1 to 54 (with the provision that the uracil may be thymine), wherein one or several nucleotides are substituted, deleted, inserted or added, wherein the nucleotides contained in the aptamer are such that,
    (i) each 2'-position of ribose of the pyrimidine nucleotide is the same or different and is a fluorine atom or substituted by atom or group selected from the group consisting of hydrogen atom, hydroxy group and methoxy group, and
    (ii) each 2'-position of ribose of the purine nucleotide is the same or different and is a hydroxy group or substituted by atom or group selected from the group consisting of hydrogen atom, methoxy group and fluorine atom;
[8] the aptamer described in [7], comprising the sequence of SEQ ID NO:58, 59 or 60;
[9] the aptamer described in [7], comprising the sequence of SEQ ID NO:40 or 44;
[10] the aptamer of any one of [1] to [9], wherein an nucleotide contained in the aptamer is modified;
[11] a complex comprising an aptamer of any one of [1] to [10] and a functional substance;
[12] the complex according to [11], wherein the functional substance is an affinity substance, a substance for labeling, an enzyme, a drug delivery vehicle or a drug;
[13] a pharmaceutical comprising an aptamer of any one of [1] to [10] or the complex described in [11] or [12];
[14] a pharmaceutical for treating or preventing an autoimmune disease, cancer, allergy, or other disease associated with inflammation, comprising the aptamer described in any one of [1] to [10] or the complex described in [11] or [12];
[15] a diagnostic reagent comprising an aptamer of any one of [1] to [10] or the complex described in [11] or [12];
[16] an IL-17 detection probe comprising an aptamer of any one of [1] to [10] or the complex described in [11] or [12];
[17] a solid phase carrier for IL-17 purification comprising an aptamer of any one of [1] to [10] or the complex described in [11] or [12];
[18] a method of detecting IL-17, comprising using an aptamer of any one of [1] to [10] or the complex described in [11] or [12]; and
[19] a method of purifying IL-17, comprising using an aptamer of any one of [1] to [10] or the complex described in [11] or [12].

Effect of the Invention

The aptamer or the complex of the present invention can be useful as a pharmaceutical or reagent such as a diagnostic reagent for inflammatory diseases, and diseases such as cancer, allergy, infectious disease and the like. The aptamer or the complex of the present invention can also be useful in purifying and concentrating IL-17, labeling of IL-17, and detecting and quantifying IL-17.

MODES FOR EMBODYING THE INVENTION

Figure 1:
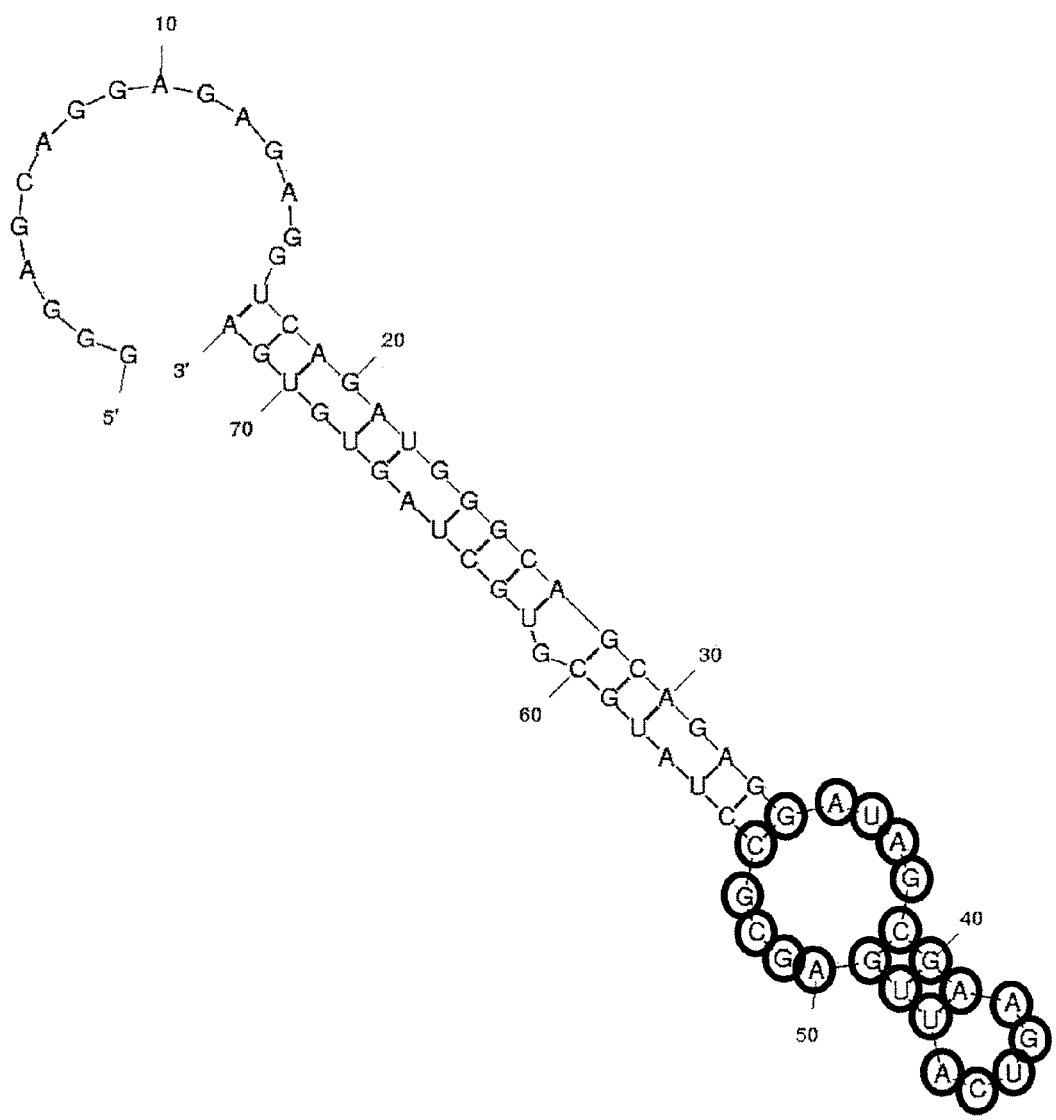
FIG. 1 shows the secondary structure of aptamer shown by SEQ ID NO: 1 predicted by the MFOLD program, wherein the part enclosed in a black circle shows a common sequence.

The present invention provides an aptamer possessing a binding activity for IL-17. The aptamers of the present invention are capable of inhibiting activities of IL-17.

An aptamer refers to a nucleic acid molecule having a binding affinity for a particular target molecule. The aptamer can also inhibit the activity of a particular target molecule by binding to the particular target molecule. The aptamer of the present invention may be an RNA, a DNA, a modified nucleic acid or a mixture thereof. The aptamer of the present invention can also be in a linear or circular form.

Inhibitory activity against IL-17 means the potential for inhibiting an optionally chosen activity possessed by IL-17. For example, IL-17 acts on immune system cells, connective tissue system cells and the like to induce the production of various cytokines and chemokines. Therefore, inhibitory activity against IL-17 refers to an activity that inhibits the production of these cytokines, chemokines and the like. Because the expression of these cytokines and chemokines induces the migration and activation of inflammatory cells, inhibitory activity against IL-17 means inhibition of the activities thereof.

IL-17 refers to a cytokine produced by Th17 cells, which are $CD4^+$ T cells, and is, for example, a protein having the amino acid sequence shown by Accession code AAH67505 or NP002181. IL-17 is sometimes called IL-17A or CTLA-8. In addition to being produced in animal bodies, IL-17 as used in the present invention can be prepared using mouse and other mammalian cells, insect cells, cells of Escherichia coli and the like, and can also be prepared by chemical synthesis. When IL-17 is prepared by cell culture or chemical synthesis, a mutant can easily be prepared. Here, a mutant means a sequence wherein several amino acids have been substituted or a partial amino acid sequence, and means a protein or peptide having at least one of the activities essentially possessed by IL-17. When an amino acid is substituted, the substituent amino acid may be a naturally occurring amino acid, or may be a non-naturally occurring amino acid. As mentioned in the present invention, IL-17 includes these mutants.

An IL-17 receptor means a cell surface protein to which IL-17 binds. As members of the IL-17 receptor family, IL-17RA, IL-17RB, IL-17RC, IL-17RD, and IL-17RE are known. As mentioned in the present invention, the IL-17 receptor may be a protein comprising a naturally occurring amino acid sequence, or may be a mutant thereof. Here, a mutant means a sequence wherein several amino acids have been substituted or a partial amino acid sequence, and means a protein or peptide possessing binding activity for IL-17. The present invention provides an aptamer that inhibits the binding of IL-17 and IL-17 receptor.

The aptamer of the present invention can exhibit inhibitory activity against IL-17 derived from any mammals. Such mammals include primates (e.g., humans, monkeys), rodents (e.g., mice, rats and guinea pigs), and companion animals, domesticated animals and work animals (e.g., dogs, cats, horses, bovines, goat, sheep, pigs).

The aptamer of the present invention is not particularly limited, as far as it is capable of binding to an optionally chosen portion of IL-17 to inhibit the activity thereof. The aptamer is preferably an aptamer that inhibits the binding of IL-17 and IL-17 receptor, comprising the sequence ggauagcgaagucauugagcgcc (SEQ ID NO:40). This sequence includes a sequence that is common to the nucleotide sequences shown by SEQ ID NOS:1, 2 and 29 described below (SEQ ID NO:58), and that has the same secondary structure as predicted using the MFOLD program (see FIG. 9).

Although the aptamer of the present invention is not particularly limited, as far as it is capable of binding to an optionally chosen portion of IL-17 to inhibit the activity thereof, it is preferably an aptamer that inhibits the binding of IL-17 and IL-17 receptor, and that comprises the sequence ggucuagccggaggagucaguaaucgguagacc (SEQ ID NO:44). This sequence includes a sequence that is common to the nucleotide sequences shown by SEQ ID NOS:6-21, 30 and 31 described below (SEQ ID NO:59) (or a sequence that is common to the nucleotide sequences shown by SEQ ID NOS: 7, 9, 13, 21 and 30 described below (SEQ ID NO:60)), and that has the same secondary structure as predicted using the MFOLD program (see FIG. 10).

Figure 2:
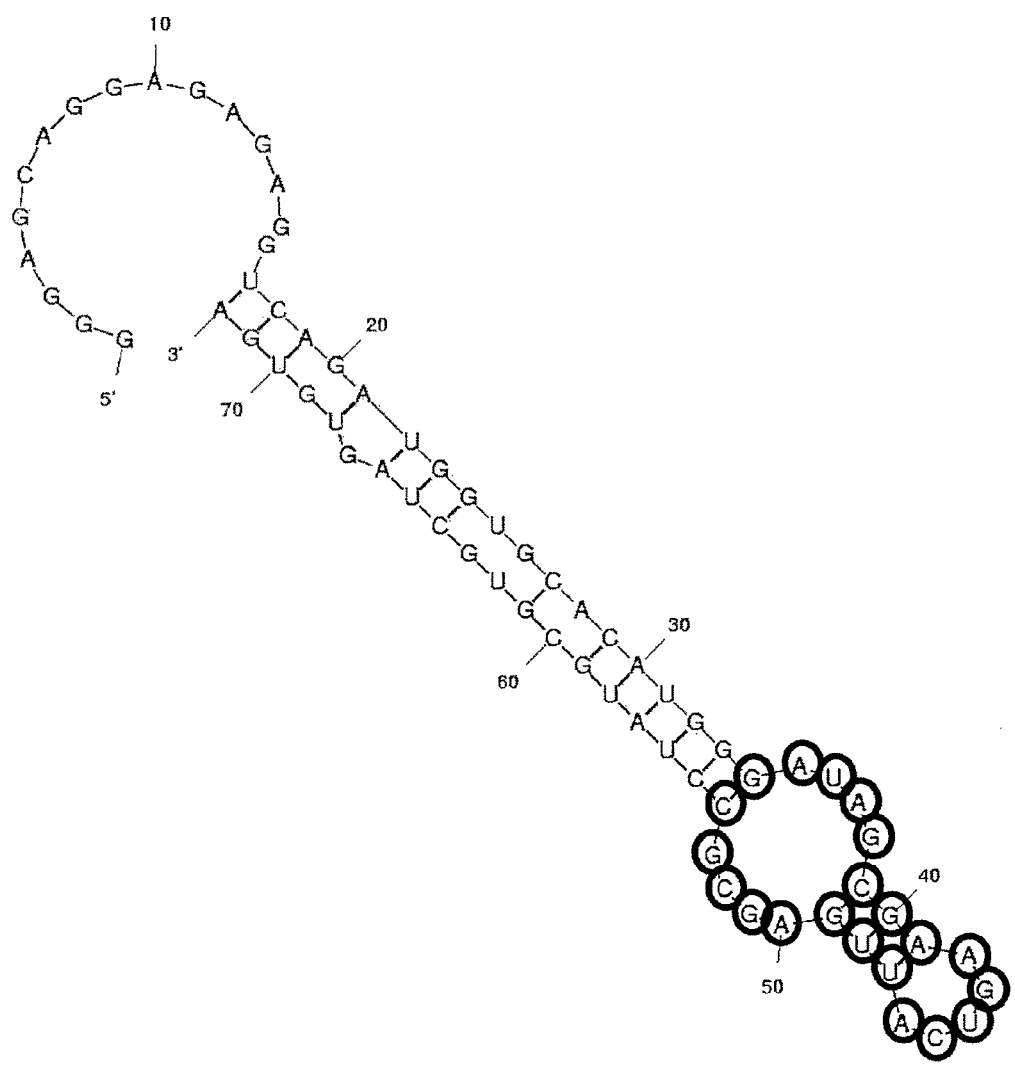
FIG. 2 shows the secondary structure of aptamer shown by SEQ ID NO: 2 predicted by the MFOLD program, wherein the part enclosed in a black circle shows a common sequence.
Figure 3:
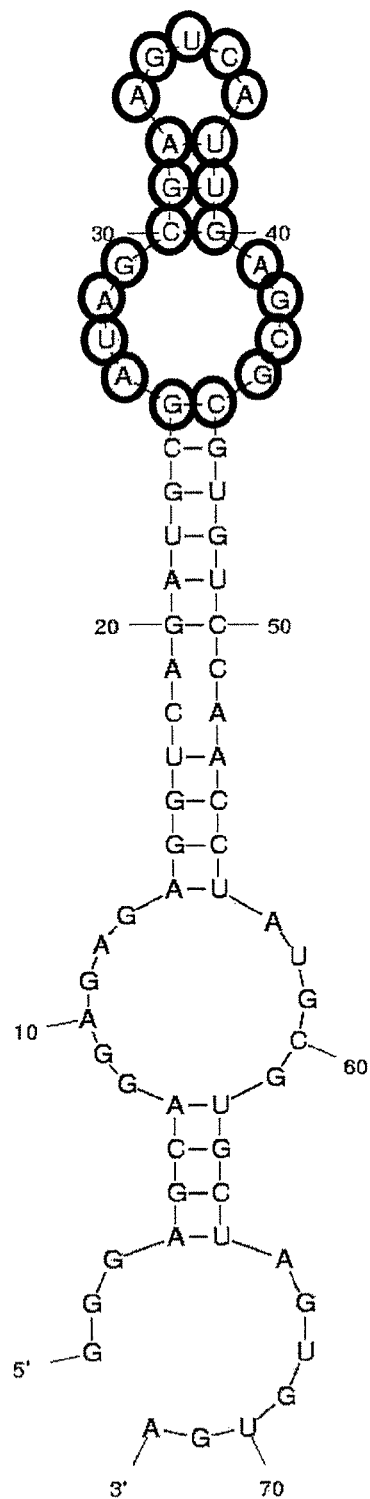
FIG. 3 shows the secondary structure of aptamer shown by SEQ ID NO: 29 predicted by the MFOLD program, wherein the part enclosed in a black circle shows a common sequence.

Although the aptamer of the present invention is not particularly limited, as far as it is capable of binding to an optionally chosen portion of IL-17 to inhibit the activity thereof, it is preferably an aptamer that inhibits the binding of IL-17 and IL-17 receptor containing the sequence gauagcgaagucauugagcgc (SEQ ID NO:58). This sequence is a sequence that is common to the nucleotide sequences shown by SEQ ID NOS:1, 2 and 29 described below, and that has the same secondary structure as predicted using the MFOLD program (see FIGS. 1-3).

Figure 4:
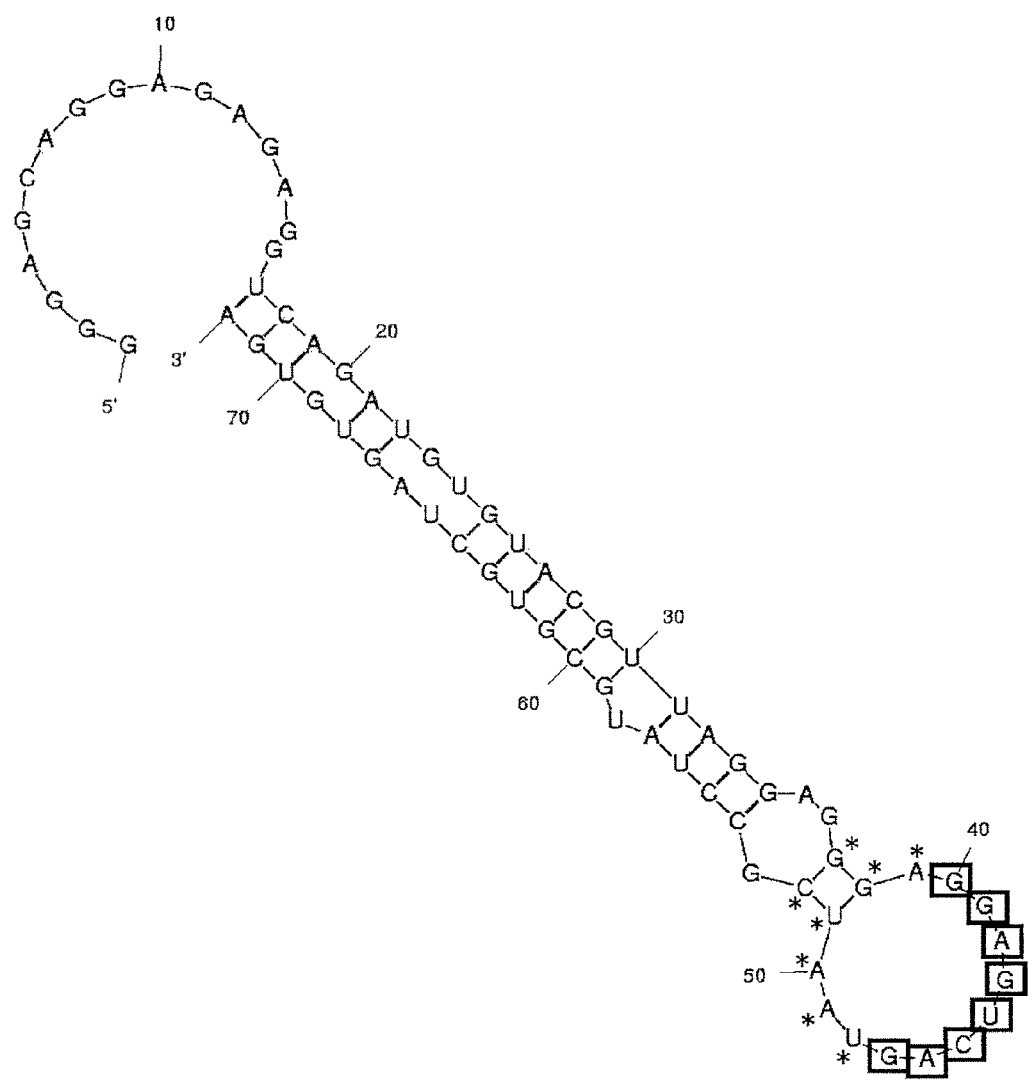
FIG. 4 shows the secondary structure of aptamer shown by SEQ ID NO: 7 predicted by the MFOLD program, wherein the part enclosed in a square and * (asterisk) shows a common sequence.
Figure 5:
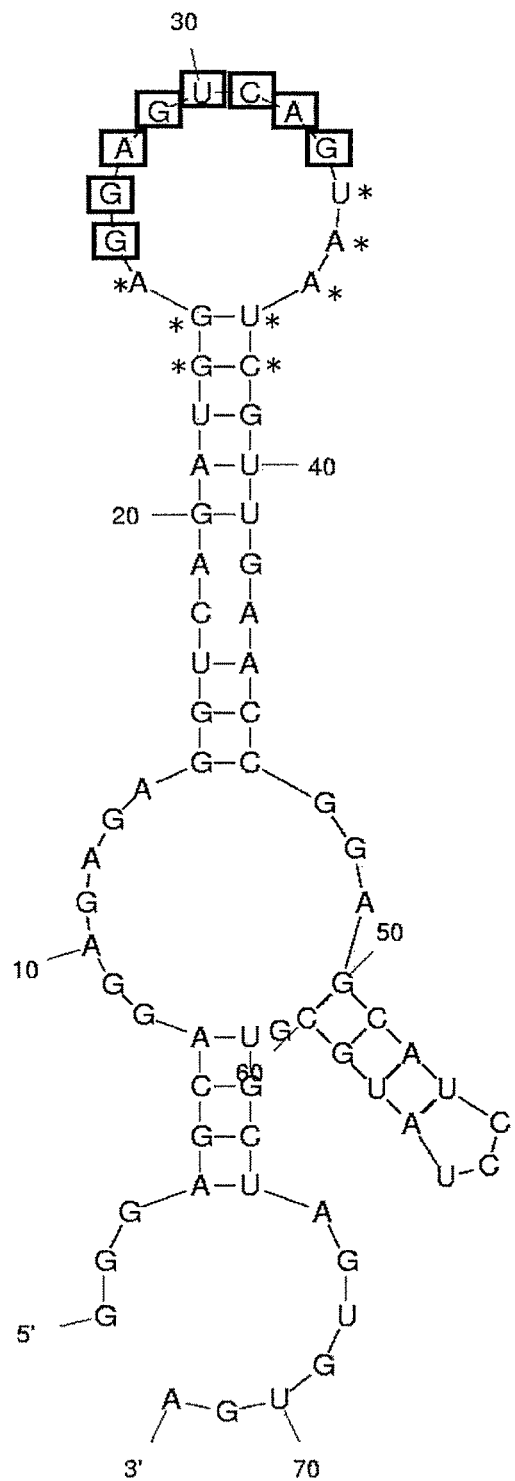
FIG. 5 shows the secondary structure of aptamer shown by SEQ ID NO: 13 predicted by the MFOLD program, wherein the part enclosed in a square and * (asterisk) shows a common sequence.
Figure 6:
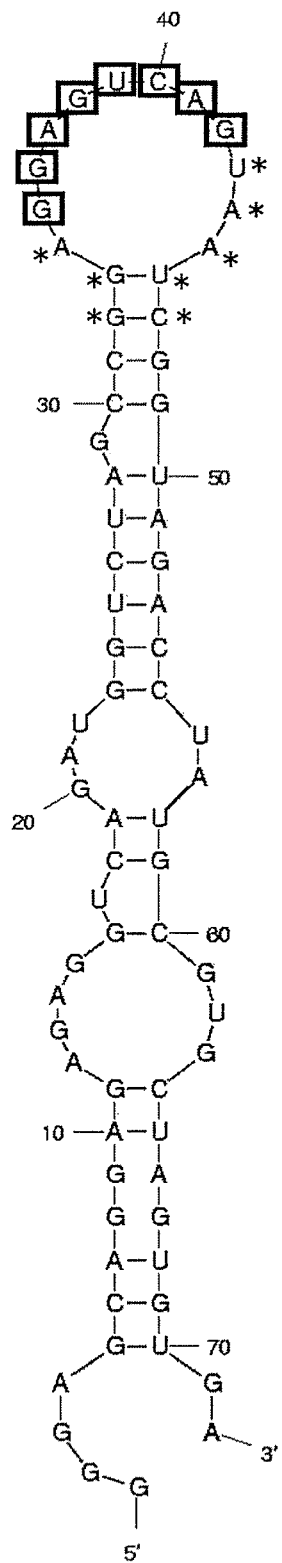
FIG. 6 shows the secondary structure of aptamer shown by SEQ ID NO: 30 predicted by the MFOLD program, wherein the part enclosed in a square and * (asterisk) show a common sequence.

Although the aptamer of the present invention is not particularly limited, as far as it is capable of binding to an optionally chosen portion of IL-17 to inhibit the activity thereof, it is preferably an aptamer that inhibits the binding of IL-17 and IL-17 receptor containing the sequence ggagucag (SEQ ID NO:59). This sequence is a sequence that is common to the nucleotide sequences shown by SEQ ID NOS:6-21, 30 and 31 described below, and that has the same secondary structure as predicted using the MFOLD program (see FIGS. 4-6).

The aptamer of the present invention is preferably an aptamer that inhibits the binding of IL-17 and IL-17 receptor, and that comprises the sequence ggaggagucaguaauc (SEQ ID NO:60). This sequence is a sequence that is common to the nucleotide sequences shown by SEQ ID NOS:7, 9, 13, 21 and 30 described below, and that has the same secondary structure as predicted using the MFOLD program (see FIGS. 4-6).

The length of the aptamer of the present invention is not limited, and can usually be about 10 to about 200 nucleotides, and can be, for example, not more than about 100 nucleotides, preferably not more than about 50 nucleotides, more preferably not more than about 40 nucleotides, most preferably not more than about 35 nucleotides. When the total number of nucleotides is smaller, chemical synthesis and mass-production will be easier, and there is a major advantage in terms of cost. It is also thought that chemical modification is easy, stability in the body is high, and toxicity is low.

Each nucleotide contained in the aptamer of the present invention is the same or different and can be a nucleotide comprising a hydroxyl group at the 2' position of ribose (e.g., ribose of pyrimidine nucleotide, ribose of purine nucleotide) (i.e., an unsubstituted nucleotide) or a nucleotide substituted (modified) by any atom or group at the 2' position of ribose (sometimes to be described as "substituted nucleotide" or "modified nucleotide" in the present invention).

As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH$_2$ group) can be mentioned. The aptamer of the present invention can also be the modified nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2' position of ribose.

In the aptamer of the present invention, all pyrimidine nucleotides are the same or different and each can be a nucleotide substituted by a fluorine atom, or a nucleotide substituted by any atom or group mentioned above, preferably an atom or group selected from the group consisting of a hydrogen atom, a hydroxyl group and a methoxy group at the 2' position of ribose.

In the aptamers of the present invention, all purine nucleotides are the same or different and each can be a nucleotide substituted by a hydroxyl group at the 2'-position of ribose, or a nucleotide substituted by any atom or group mentioned above, preferably an atom or a group selected from the group consisting of a hydrogen atom, a methoxy group, and a fluorine atom at the 2'-position of ribose.

The aptamer of the present invention can also be one wherein all nucleotides identically comprise a hydroxyl group, or any atom or group mentioned above, for example, the identical group selected by the group consisting of a hydrogen atom, a fluorine atom, a hydroxyl group and a —O-Me group, at the 2' position of ribose.

The aptamer of the present invention can also possess the feature of being capable of inhibiting the activity of IL-17, but not capable of inhibiting the activity of IL-17F. The aptamer of the present invention can also possess the feature of being capable of inhibiting the binding of IL-17 and IL-17 receptor, but not capable of inhibiting the binding of IL-17F and IL-17 receptor. IL-17F is a protein of the IL-17 family having a homology of 44%, being most similar to IL-17.

The aptamer of the present invention can also be:
(a) an aptamer comprising a nucleotide sequence selected from among SEQ ID NO:1-54 (with the provision that the uracil may be thymine);
(b) an aptamer comprising a nucleotide sequence selected from among SEQ ID NO:1-54 (with the provision that the uracil may be thymine), wherein one to several nucleotides are substituted, deleted, inserted or added; or
(c) a conjugate selected from the group consisting of plural conjugates of aptamers (a) above, plural conjugates of aptamers (b) above, and plural conjugates of aptamers (a) and (b) above.

Preferred of the (a)-(c) above are (a)-(c) wherein the nucleotide sequence selected from among SEQ ID NOS:1-54 is the sequence of SEQ ID NO:58, 59 or 60.

Preferred of the (a)-(c) above are (a)-(c) wherein the nucleotide sequence selected from among SEQ ID NOS:1-54 is the sequence of SEQ ID NO:40 or 44.

In (b) above, there is no limitation on the number of nucleotides substituted, deleted, inserted or added. The number of nucleotides can be, for example, not more than about 30, preferably not more than about 20, more preferably not more than about 10, still more preferably not more than 5, most preferably 4, 3, 2 or 1. In (c) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described plural conjugates is not particularly limited, as long as it is two or more, and the plurality can be, for example, 2, 3 or 4.

Each of the nucleotides in (a) to (c) above, whether the same or different, can be a nucleotide comprising a hydroxyl group at the 2' position of ribose, or a nucleotide substituted by any groups (e.g., hydrogen atom, fluorine atom or —O-Me group) at the 2' position of ribose (e.g., ribose of pyrimidine nucleotide).

For example, the aptamer of the present invention may be an aptamer wherein the nucleotides contained in the (a)-(c) above are such that:
(i) each 2'-position of ribose of the pyrimidine nucleotide is the same or different and is substituted by a fluorine atom or substituted by any atom or group mentioned above, preferably atom or group selected from the group consisting of hydrogen atom, hydroxy group and methoxy group; and
(ii) each 2'-position of ribose of the purine nucleotide is the same or different and is substituted by hydroxy group or substituted by any atom or group mentioned above, preferably atom or group selected from the group consisting of hydrogen atom, methoxy group and fluorine atom. The present invention also provides the above-described aptamer.

The aptamer of the present invention may be one wherein a sugar residue (e.g., ribose) of each nucleotide has been modified to increase the IL-17 binding activity, stability, drug deliverability and the like. As examples of the modification in a sugar residue, replacement of oxygen atom at the 2'-position, 3'-position and/or 4'-position of the sugar residue with another atom, and the like can be mentioned. As the kind of the modification, fluorination, O-alkylation (e.g., O-methylation, O-ethylation), O-arylation, S-alkylation (e.g., S-methylation, S-ethylation), S-arylation, and amination (e.g., —NH$_2$) can be mentioned. Such alterations in the sugar residue can be performed by a method known per se (see, for example, Sproat et al., (1991) Nucl. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the binding activity to IL-17 and the like. As examples of such alterations, pyrimidine alteration at 5-position, purine alteration at 6- and/or 8-position(s), alteration with an extracyclic amine, substitution with 4-thiouridine, and substitution with 5-bromo or 5-iodo-uracil can be mentioned. The phosphate group contained in the aptamer of the present invention may be altered to confer resistance to nuclease and hydrolysis. For example, the P(O)O group may be substituted with P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—) [wherein each unit of R or R' is independently H or a substituted or unsubstituted alkyl (e.g., methyl, ethyl)].

The joining group is, for example, —O—, —N— or —S—, and nucleotides can bind to an adjoining nucleotide via these joining groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

The aptamer of the present invention can be chemically synthesized as disclosed herein and by a method known per se in the art. An aptamer binds to the target molecule in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target molecule can be substituted. In particular, because the region of stem structure has already formed base pairs and faces the inside of the double helical structure, nucleic acid bases are unlikely to bind directly to the target molecule. Therefore, even when a base pair is replaced with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change widely.

An aptamer can be prepared by utilizing the SELEX method or an improved version thereof (for example, Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target molecule, but this does not mean binding of a bioactive site of the target molecule. Therefore, the aptamers obtained by SELEX do not necessarily act on the function of the target substance. IL-17 is a basic protein, and is thought to be likely to allow nucleic acids to bind thereto nonspecifically. An aptamer that does not bind to an active site does not influence the activity of the target substance. In fact, the RNA used for control did not inhibit the binding of IL-17 and IL-17 receptor.

The thus-selected active aptamer can be subjected to SELEX optimization to achieve high function. For SELEX optimization, a template wherein an aptamer with a determined sequence is partially randomized or a template doped with about 10 to 30% of random sequences is prepared, and SELEX is performed again.

An aptamer obtained by SELEX has a length of about 70 nucleotides, and this is difficult to prepare as a pharmaceutical as it is. Hence, it is necessary to repeat try-and-error efforts to shorten the aptamer to a length of about 50 nucleotides or less enabling easy chemical synthesis.

Depending on the primer design for an aptamer obtained by SELEX, the ease of the subsequent minimization operation changes. Unless the primer is designed successfully, subsequent development will be impossible even if an aptamer with activity is selected by SELEX. In the present invention, it has been found that an aptamer retaining activity even with 23 nucleotides (SEQ ID NO: 40) or 33 nucleotides (SEQ ID NO: 44) can be obtained, and these sequences are particularly important for binding with IL-17.

Aptamers are easily modifiable because they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the obtained aptamer with the target molecule is identified by repeated try-and-error efforts as described above, the activity remains unchanged in many cases even when a new sequence is added to both ends of the sequence. The length of the new sequence is not particularly limited.

Modifications, like sequences, afford a wide range of design or alterations.

As stated above, aptamers permit a wide range of design or alterations of modifications. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:
Primer sequence (i)-(N)a-fixed sequence-(N)b-Primer sequence (ii)
[wherein (N)a represents a nucleotide chain consisting of "a" units of N; (N)$_b$ represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or complex of the present invention can be used as, for example, a pharmaceutical, diagnostic drug, examination drug, or reagent. The same is particularly useful as a pharmaceutical, diagnostic drug, examination drug, or reagent for autoimmune diseases and diseases accompanied by inflammation.

Here, autoimmune diseases and diseases accompanied by inflammation include multiple sclerosis, systemic lupus erythematosus (SLE), scleroderma, Sjögren syndrome, polymyositis (PM), dermatomyositis (DM), rheumatic arthritis (chronic rheumatoid arthritis (RA), osteoarthritis (OA)), inflammatory enterocolitis (Crohn disease and the like), progressive systemic sclerosis (PSS), periarthritis nodosa (PN), thyroid diseases (Basedow disease and the like), Guillain-Barré syndrome, primary biliary cirrhosis (PBC), idiopathic thrombocytopenic purpura, autoimmune hemolytic anemia, myasthenia gravis (MG), amyotrophic lateral sclerosis (ALS), type I diabetes, psoriasis, asthma, neutrophil functional abnormalities, eosinophilic pneumonia, sudden pulmonary fibrosis, hypersensitivity pneumonitis, esophageal cancer, thyroid cancer, bladder cancer, colorectal cancer, gastric cancer, pancreatic cancer, chest cancer, liver cancer, lung cancer, non-small cell lung cancer, breast cancer, neuroblastoma, neuroglastoma, glioblastoma, uterine cancer, uterine cervical cancer, ovarian cancer, Wilms tumor, prostatic cancer, graft rejections in transplantation, graft-versus-host disease, asthma, allergic rhinitis, atopic dermatitis, food hypersensitivity, urticaria, postoperative adhesion, endometriosis, adult periodontitis, bronchitis, COPD, infectious diseases and the like. In particular, multiple sclerosis, rheumatic arthritis, inflammatory enterocolitis, scleroderma, asthma, and graft-versus-host disease can be mentioned.

The aptamer or complex of the present invention can also be used as a drug delivery vehicle, a probe for in vivo imaging, a probe for determination of blood concentrations of IL-17, a probe for histological staining, a probe for ELISA, and a ligand for separation and purification of IL-17.

IL-17 is known to act on various cells such as fibroblasts, endothelial cells, epithelial cells, chondrocytes, osteoblasts, dendritic cell progenitor cells, marrow-derived interstitial cells, T cells, macrophages, and neutrophils. IL-17 induces the production and expression of various cytokines, chemokines, and receptors by acting on these cells. Specifically, CXCL1 (KC or Groα), CXCL2 (MIP2 or Groβ), CXCL5 (LIX), CXCL6 (GCP-2), CXCL8 (IL-8), CXCL9 (MIG), CXCL10 (IP10), CXCL11 (1-TAC), CCL2 (MCP-1), CCL5 (RANTES), CCL7 (MCP-3), CCL11 (Eotaxin), CXCL12 (SDF-1), CCL20 (MIP3α), IL-1, IL-6, IL-8, IL-19, TNF, CSF2 (GM-CSF), CSF3 (G-CSF), ICAM-1, VCAM-1, PTGS2 (COX2), NOS2 (iNOS), LCN2 (24p3), DEFB4 (BD2), S100A7 (Psoriasin), S100A8 (Calgranulin A), S100A9 (Calgranulin B), MUC5AC, MUC5B, EREG, SOCS3, TNFSF11 (RANKL), MMP1, MMP3, MMP9, MMP13, TIMP1, ADAMTS4, PGE2, SCF, CD80, CD86, MHC and the like can be mentioned. Therefore, the aptamer or complex of the present invention can be used as a pharmaceutical, diagnostic drug, examination drug, or reagent for diseases associated with these cells and cytokines, chemokines and the like.

By binding to a receptor thereof, IL-17 activates Act1 and TRAF6, and activates the NF-κB pathway, MAP kinase pathway, C/EBP pathway and the like. Therefore, the aptamer or complex of the present invention can be used as a pharmaceutical, diagnostic drug, examination drug, or reagent for diseases associated with the activation of these signal transduction pathways.

The aptamer or complex of the present invention can also be used to prevent or treat a broad range of diseases, including autoimmune diseases (e.g., multiple sclerosis, systemic lupus erythematosus (SLE), scleroderma, Sjögren syndrome, polymyositis (PM), dermatomyositis (DM), rheumatic arthritis (chronic rheumatoid arthritis (RA), osteoarthritis (OA)), inflammatory enterocolitis (Crohn disease and the like), progressive systemic sclerosis (PSS), periarthritis nodosa (PN), thyroid diseases (Basedow disease and the like), Guillain-Barré syndrome, primary biliary cirrhosis (PBC), idiopathic thrombocytopenic purpura, autoimmune hemolytic anemia, myasthenia gravis (MG), amyotrophic lateral sclerosis (ALS), type I diabetes, psoriasis, asthma, neutrophil functional abnormalities, eosinophilic pneumonia, sudden pulmonary fibrosis, hypersensitivity pneumonitis), cancers (e.g., esophageal cancer, thyroid cancer, bladder cancer, colorectal cancer, gastric cancer, pancreatic cancer, chest cancer, liver cancer, lung cancer, non-small cell lung cancer, breast cancer, neuroblastoma, neuroglastoma, glioblastoma, uterine cancer, uterine cervical cancer, ovarian cancer, Wilms tumor, prostatic cancer), transplantation diseases (e.g., graft rejections, graft-versus-host disease), allergies (e.g., asthma, allergic rhinitis, atopic dermatitis, food hypersensitivity, urticaria), other inflammation-related diseases (e.g., postoperative adhesion, endometriosis, adult periodontitis, bronchitis, COPD), infectious diseases and the like. In particular, the aptamer of the present invention can be used to prevent or treat multiple sclerosis, rheumatic arthritis, inflammatory enterocolitis, scleroderma, asthma, and graft-versus-host disease.

The pharmaceutical of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The pharmaceutical of the present invention can be coated by a method known per se for the purpose of taste masking, enteric dissolution, sustained release and the like. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., red iron oxide, titanium dioxide and the like) and the like are used. The pharmaceutical may be a rapid-release preparation or sustained-release preparation. Examples of sustained-release bases include liposome, atelocollagen, gelatin, hydroxyapatite, PLGA and the like.

As preparations suitable for parenteral administration (for example, intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethyleneglycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monoleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer or complex of the present invention, blending it in an inhalation propellant and/or carrier, and filling them in an appropriate inhalation vessel. When the above-described aptamer or complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer or the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying IL-17.

The aptamer or the complex of the present invention can be immobilized onto a solid phase carrier by a method known per se. For example, a method that introduces an affinity substance (e.g., those described above) or a predetermined functional group into the aptamer or the complex of the present invention, and then immobilizing the aptamer or complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating IL-17. In particular, the present invention makes it possible to separate IL-17 from the proteins of other family proteins. The method of purification and concentration of the present invention can comprise adsorbing IL-17 to the solid phase carrier of the present invention, and eluting the adsorbed IL-17 with an eluent. Adsorption of IL-17 to the solid phase carrier of the present invention can be achieved by a method known per se. For example, a IL-17-containing sample (e.g., bacterial or cell culture or culture supernatant, blood) is introduced into the solid phase carrier of the present invention or a composition containing the same. IL-17 can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, a potassium salt (e.g., NaCl, KCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after IL-17 adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The aptamer or complex of the present invention can be utilized as a detection probe, particularly as a probe for detection of IL-17. The method of labeling the aptamer is not particularly limited; methods known per se can be applied. Such methods include, for example, labeling with a radioisotope, labeling with a fluorescent dye or fluorescent protein, and the like.

The present invention also provides a method of detecting and quantifying IL-17. In particular, the present invention makes it possible to detect and quantify IL-17 separately from the proteins of other family proteins. The method of detection and quantitation of the present invention can comprise measuring IL-17 by utilizing the aptamer of the present invention (e.g., by the use of the complex and solid phase carrier of the present invention). The method of detecting and quantifying IL-17 can be performed in the same manner as an immunological method, except that the aptamer of the present invention is used in place of an antibody. Therefore, by using the aptamer of the present invention as a probe in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), use in place of a secondary antibody in Western blot technique, immunohistochemical staining method, and cell sorting method, detection and quantitation can be performed. These methods can be useful in, for example, measuring IL-17 contents in living organisms or biological samples, and in diagnosing a disease associated with IL-17.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1

Preparation of Nucleic Acids that Bind Specifically to IL-17

Nucleic acids that bind specifically to IL-17 were prepared using the SELEX method. SELEX was performed with improvements of the method of Ellington et al. (Ellington and Szostak, Nature 346, 818-822, 1990) and the method of Tuerk et al. (Tuerk and Gold, Science 249, 505-510, 1990). Human IL-17 (produced by Peprotech Company) was used as a target substance. IL-17 was immobilized on an agarose resin (NHS-activated Sepharose, produced by GE Healthcare) by amino coupling. The amino coupling was performed as directed in the specifications by GE Healthcare Company. The amount immobilized was confirmed by examining the IL-17 solution before immobilization and the supernatant just after immobilization by SDS-PAGE. As a result of the SDS-PAGE, no band of IL-17 was detected in the supernatant; it was confirmed that nearly all of the IL-17 used had been coupled. This means that about 400 pmol of IL-17 was immobilized to about 10 μL of the resin.

The RNA used in the first round (30N-RNA) was obtained by transcribing a chemically synthesized DNA using the DuraScribe™ T7 Transcription Kit (manufactured by Epicentre). The RNA obtained by this method has the 2'-position of ribose of the pyrimidine nucleotide fluoro-substituted. The following DNA of 89 nucleotides long, having a primer sequence at each end of a 30-nucleotide random sequence, was used as a DNA template. The DNA template and primers used were prepared by chemical synthesis. The DNA template and primers used are shown below.

```
DNA template:
                                        (SEQ ID NO: 55)
5'-tcacactagcacgcatagg-30N-catctgacctctctcctgc tccc-3'

Primer Fwd:
                                        (SEQ ID NO: 56)
5'-taatacgactcactatagggagcaggagagaggtcagatg-3'

Primer Rev:
                                        (SEQ ID NO: 57)
5'-tcacactagcacgcatagg-3'
```

N represents any one of A, G, C and T. The primer Fwd comprises a promoter sequence of T7 RNA polymerase. The variation of the RNA pool used in the first round was theoretically $10^{14}$.

The RNA pool was added to the resin with IL-17 immobilized thereon, and allowed to stand at room temperature for 30 minutes. After the 30 minutes, the resin was washed with solution A to remove the RNA not bound to IL-17. Here, the solution A is a mixed solution of 145 mM sodium chloride, 5.4 mM potassium chloride, 1.8 mM calcium chloride, 0.8 mM magnesium chloride, 20 mM Tris (pH 7.6), and 0.05% Tween 20. The RNA bound to IL-17 was recovered by stirring with the addition of an eluent at room temperature for 10 minutes. The solution A was used as the eluent after being adjusted to pH 7.6 by the addition of 6 M guanidine hydrochloride. The recovered RNA was amplified by RT-PCR and transferred using the DuraScribe™ T7 Transcription Kit, and this was used as the pool for the next round. Each round of these steps was repeated in 8 rounds. After completion of SELEX, the PCR product was cloned into the pGEM-T Easy vector (produced by Promega), and the *Escherichia coli* strain DH5α (produced by Toyobo) was transformed therewith. After the plasmid was extracted from a single colony, 48 clones were examined for base sequence using a DNA sequencer (3130×1 Genetic Analyzer, produced by ABI).

After SELEX was performed in 6 rounds, the sequences were examined; sequence convergence was seen. There existed 11 sequences shown by SEQ ID NO:1, and one sequence with a 2-base substitution was present. There existed six sequences shown by SEQ ID NO:2. There existed two sequences shown by SEQ ID NOS:3-6. There existed one sequence shown by SEQ ID NOS:7-28. In the sequences shown by SEQ ID NOS:1 and 2, the common sequence gauagcgaagucauugagcgc (SEQ ID NO:58; 21 nucleotides) was contained. In the sequences shown by SEQ ID NOS:6-21, the common sequence ggagucag (SEQ ID NO:59; 8 nucleotides) was contained. When the secondary structures of the sequences shown by SEQ ID NOS:1 and 2 were predicted using the MFOLD program (M. Zuker, Nucleic Acids Res. 31(13), 3406-3415, 2003), the common sequence portions were found to be morphologically identical (see FIGS. 1 and 2).

Next, the sequences obtained after the eight rounds of SELEX were examined. Greater convergence was observed than with the six rounds; there existed 25 and 7 sequences shown by SEQ ID NOS:1 and 2, respectively. There existed one sequence resulting from 2-base substitution of the sequence shown by SEQ ID NO:1, and there existed one sequence resulting from 1-base substitution of the sequence shown by SEQ ID NO:2. There existed four, three, and two sequences shown by SEQ ID NOS:29-31, respectively. There existed one sequence shown by SEQ ID NOS:32-36. The sequence shown by SEQ ID NO:29 comprised the common sequence SEQ ID NO:58. When the secondary structure of the sequence shown by SEQ ID NO:29 was predicted using the MFOLD program, the common sequence portion was found to be morphologically identical to the common sequence contained in the sequences shown by SEQ ID NOS:1 and 2 (see FIG. 3). The sequences shown by SEQ ID NOS:30 and 31 contained the common sequence of SEQ ID NO:59. Furthermore, the sequences shown by SEQ ID NOS: 7, 9, 13, 21 and 30 contained the common sequence ggaggagucaguaauc (SEQ ID NO:60; 16 nucleotides). The common sequence shown by SEQ ID NO:60 comprises SEQ ID NO:59. When the secondary structures of these sequences were predicted using the MFOLD program, the common sequence portions were found to be morphologically identical (see FIGS. 4-6). The bases of the common sequence shown by SEQ ID NO:59 are enclosed in squares, and the bases of the remaining sequence of the common sequence shown by SEQ ID NO:60 are marked with *s (asterisks).

Shown below are the respective nucleotide sequences. The parenthesis for each nucleotide indicates a modification at the 2'-position of ribose. F represents a fluorine atom, and M represents OMe. Specifically, c(F) represents cytidine wherein the 2'-position of ribose is substituted by a fluorine atom, and u(F) represents uridine wherein the 2'-position of ribose is substituted by a fluorine atom. a(M) represents adenosine wherein the 2'-position of ribose is substituted by OMe, g(M) represents guanosine wherein the 2'-position of ribose is substituted by OMe, and c(M) represents cytidine wherein the 2'-position of ribose is substituted by OMe (the same applies below).

The beginning of each sequence is the 5' end, and the terminus is the 3' end.

SEQ ID NO: 1:
gggagc(F)aggagagaggu(F)c(F)agau(F)gggc(F)agc(F)a gaggau(F)agc(F)gaagu(F)c(F)au(F)u(F)gagc(F)gc(F)

c(F)u(F)au(F)gc(F)gu(F)gc(F)u(F)agu(F)gu(F)ga

Figure 7:
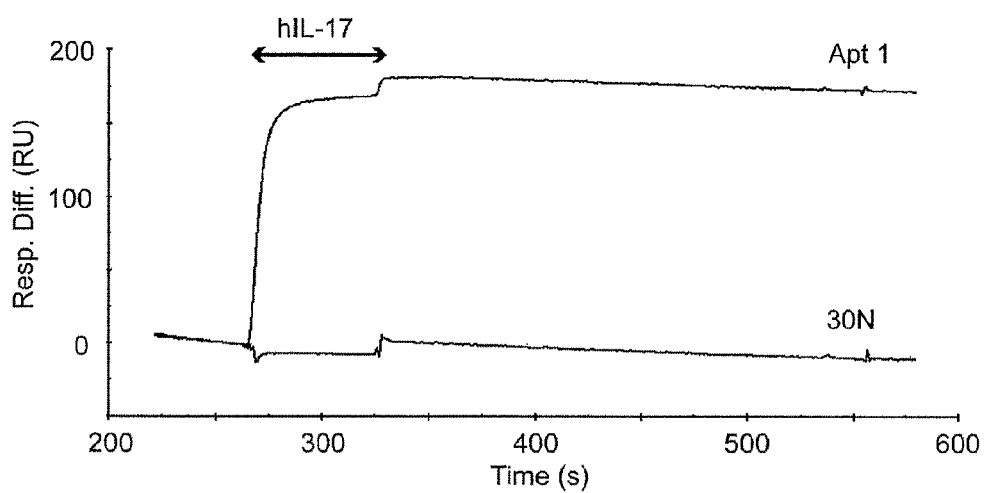
FIG. 7 is a sensorgram showing that the aptamer shown by SEQ ID NO:1 (Apt1) binds to human IL-17.

SEQ ID NO: 2:
gggagc(F)aggagagaggu(F)c(F)agau(F)ggu(F)gc(F)ac (F)au(F)gggau(F)agc(F)gaagu(F)c(F)au(F)u(F)gagc (F)gc(F)c(F)u(F)au(F)gc(F)gu(F)gc(F)u(F)agu(F)gu (F)ga SEQ ID NO: 3:
gggagc(F)aggagagaggu(F)c(F)agau(F)gu(F)gu(F)aagg u(F)c(F)ggaagu(F)c(F)au(F)gaac(F)ggc(F)c(F)c(F)g gac(F)c(F)u(F)au(F)gc(F)gu(F)gc(F)u(F)agu(F)gu (F)ga SEQ ID NO: 4:
gggagc(F)aggagagaggu(F)c(F)agau(F)gc(F)u(F)au(F)

agc(F)gaagu(F)c(F)au(F)u(F)gagc(F)gagac(F)au(F)a ggc(F)c(F)u(F)au(F)gc(F)gu(F)gc(F)u(F)agu(F)gu (F)ga -continued SEQ ID NO: 5:
gggagc(F)aggagagaggu(F)c(F)agau(F)gagc(F)gc(F)c
(F)au(F)agggu(F)agagaagc(F)c(F)au(F)u(F)gau(F)c
(F)ac(F)c(F)u(F)au(F)gc(F)gu(F)gc(F)u(F)agu(F)gu
(F)ga SEQ ID NO: 6:
gggagc(F)aggagagaggu(F)c(F)agau(F)ggu(F)gau(F)gc
(F)au(F)aggagu(F)ggagu(F)c(F)agau(F)au(F)agc(F)c
(F)c(F)u(F)au(F)gc(F)gu(F)gc(F)u(F)agu(F)gu(F)ga SEQ ID NO: 7
gggagc(F)aggagagaggu(F)c(F)agau(F)gu(F)gu(F)ac
(F)gu(F)u(F)aggagggaggagu(F)c(F)agu(F)aau(F)c(F)
gc(F)c(F)u(F)au(F)gc(F)gu(F)gc(F)u(F)agu(F)gu(F)
ga SEQ ID NO: 8
gggagc(F)aggagagaggu(F)c(F)agau(F)ggaggagu(F)c
(F)agc(F)aau(F)c(F)gu(F)u(F)ggc(F)c(F)u(F)u(F)c
(F)u(F)gc(F)gac(F)c(F)u(F)au(F)gc(F)gu(F)gc(F)u
(F)agu(F)gu(F)ga SEQ ID NO: 9
gggagc(F)aggagagaggu(F)c(F)agau(F)ggaggagu(F)c
(F)agu(F)aau(F)c(F)gu(F)u(F)ggc(F)c(F)c(F)u(F)gc
(F)u(F)u(F)c(F)ac(F)c(F)u(F)au(F)gc(F)gu(F)gc(F)
u(F)agu(F)gu(F)ga SEQ ID NO: 10
gggagc(F)aggagagaggu(F)c(F)agau(F)ggaggagu(F)c
(F)agu(F)gau(F)c(F)agu(F)gac(F)c(F)u(F)c(F)u(F)u
(F)gu(F)ggc(F)c(F)u(F)au(F)gc(F)gu(F)gc(F)u(F)ag
u(F)gu(F)ga SEQ ID NO: 11
gggagc(F)aggagagaggu(F)c(F)agau(F)ggu(F)ggagu(F)
c(F)agu(F)gagc(F)gu(F)u(F)gac(F)c(F)ggc(F)aau(F)
c(F)ac(F)c(F)u(F)au(F)gc(F)gu(F)gc(F)u(F)agu(F)g
u(F)ga SEQ ID NO: 12
gggagc(F)aggagagaggu(F)c(F)agau(F)ggaggagu(F)c
(F)agu(F)gau(F)c(F)gu(F)u(F)gc(F)c(F)ggac(F)u(F)
u(F)gc(F)c(F)c(F)c(F)u(F)au(F)gc(F)gu(F)gc(F)u
(F)agu(F)gu(F)ga SEQ ID NO: 13
gggagc(F)aggagagaggu(F)c(F)agau(F)ggaggagu(F)c
(F)agu(F)aau(F)c(F)gu(F)u(F)gaac(F)c(F)ggagc(F)a
u(F)c(F)c(F)u(F)au(F)gc(F)gu(F)gc(F)u(F)agu(F)gu
(F)ga SEQ ID NO: 14
gggagc(F)aggagagaggu(F)c(F)agau(F)gau(F)gac(F)ag
gagu(F)c(F)agau(F)au(F)au(F)gc(F)ac(F)au(F)u
(F)gac(F)c(F)u(F)au(F)gc(F)gu(F)gc(F)u(F)agu(F)g
u(F)ga SEQ ID NO: 15
gggagc(F)aggagagaggu(F)c(F)agau(F)ggu(F)u(F)aggu
(F)ggagu(F)c(F)agggaaaaaac(F)c(F)gu(F)u(F)u(F)gc
(F)c(F)u(F)au(F)gc(F)gu(F)gc(F)u(F)agu(F)gu(F)ga SEQ ID NO: 16
gggagc(F)aggagagaggu(F)c(F)agau(F)gu(F)agagu(F)g
gagu(F)c(F)agau(F)au(F)agc(F)c(F)u(F)ac(F)aagu
(F)c(F)c(F)c(F)u(F)au(F)gc(F)gu(F)gc(F)u(F)agu
(F)gu(F)ga SEQ ID NO: 17
gggagc(F)aggagagaggu(F)c(F)agau(F)gu(F)aau(F)agg
ggagu(F)c(F)agau(F)au(F)ac(F)c(F)aac(F)gaagac(F)
c(F)u(F)au(F)gc(F)gu(F)gc(F)u(F)agu(F)gu(F)ga SEQ ID NO: 18
gggagc(F)aggagagaggu(F)c(F)agau(F)gu(F)aggu(F)gu
(F)gagu(F)ggagu(F)c(F)agaaau(F)agc(F)c(F)gc(F)ac
(F)c(F)u(F)au(F)gc(F)gu(F)gc(F)u(F)agu(F)gu(F)ga SEQ ID NO: 19
gggagc(F)aggagagaggu(F)c(F)agau(F)gc(F)gau(F)c
(F)gu(F)ac(F)gc(F)gggggggagu(F)c(F)agau(F)au(F)
ac(F)c(F)u(F)au(F)gc(F)gu(F)gc(F)u(F)agu(F)gu(F)
ga SEQ ID NO: 20
gggagc(F)aggagagaggu(F)c(F)agau(F)gu(F)gau(F)agu
(F)ac(F)gc(F)ggaagggagu(F)c(F)agau(F)au(F)ac(F)
c(F)u(F)au(F)gc(F)gu(F)gc(F)u(F)agu(F)gu(F)ga SEQ ID NO: 21
gggagc(F)aggagagaggu(F)c(F)agau(F)gc(F)aaggaggag
u(F)c(F)agu(F)aau(F)cF)gu(F)gac(F)au(F)u(F)ggc
(F)c(F)c(F)u(F)au(F)gc(F)gu(F)gc(F)u(F)agu(F)gu
(F)ga SEQ ID NO: 22
gggagc(F)aggagagaggu(F)c(F)agau(F)gc(F)u(F)au(F)
gc(F)c(F)gc(F)ac(F)aaac(F)ac(F)gu(F)au(F)gagu(F)
gc(F)u(F)c(F)ac(F)c(F)u(F)au(F)gc(F)gu(F)gc(F)u
(F)agu(F)gu(F)ga SEQ ID NO: 23
gggagc(F)aggagagaggu(F)c(F)agau(F)ggu(F)u(F)ac
(F)u(F)u(F)c(F)c(F)c(F)aaaagu(F)c(F)au(F)aaau(F)
ggggu(F)u(F)ac(F)c(F)u(F)au(F)gc(F)gu(F)gc(F)u
(F)agu(F)gu(F)ga SEQ ID NO: 24
gggagc(F)aggagagaggu(F)c(F)agau(F)ggaggagac(F)ag
u(F)aau(F)c(F)gu(F)u(F)gac(F)c(F)gc(F)u(F)u(F)c
(F)gu(F)gc(F)c(F)u(F)au(F)gc(F)gu(F)gc(F)u(F)agu
(F)gu(F)ga SEQ ID NO: 25
gggagc(F)aggagagaggu(F)c(F)agau(F)gu(F)gau(F)agc
(F)gaaggc(F)au(F)u(F)gagc(F)gc(F)ac(F)au(F)u(F)a
aac(F)c(F)u(F)au(F)gc(F)gu(F)gc(F)u(F)agu(F)gu
(F)ga SEQ ID NO: 26
gggagc(F)aggagagaggu(F)c(F)agau(F)gggc(F)agc(F)a
gaggau(F)gc(F)gaagu(F)c(F)au(F)u(F)gagc(F)gc(F)c
(F)u(F)au(F)gc(F)gu(F)gc(F)u(F)agu(F)gu(F)ga SEQ ID NO: 27
gggagc(F)aggagagaggu(F)c(F)agau(F)gc(F)c(F)u(F)g
gu(F)aggc(F)gu(F)agagaagu(F)c(F)au(F)u(F)gau(F)c
(F)agc(F)c(F)u(F)au(F)gc(F)gu(F)gc(F)u(F)agu(F)g
u(F)ga SEQ ID NO: 28
gggagc(F)aggagagaggu(F)c(F)agau(F)gu(F)u(F)au(F)
aaaagc(F)u(F)u(F)aagu(F)gc(F)u(F)gu(F)c(F)aac(F)
u(F)u(F)c(F)u(F)ac(F)c(F)u(F)au(F)gc(F)gu(F)gc
(F)u(F)agu(F)gu(F)ga SEQ ID NO: 29:
gggagc(F)aggagagaggu(F)c(F)agau(F)gc(F)gau(F)agc
(F)gaagu(F)c(F)au(F)u(F)gagc(F)gc(F)gu(F)gu(F)c
(F)c(F)aac(F)c(F)u(F)au(F)gc(F)gu(F)gc(F)u(F)agu
(F)gu(F)ga SEQ ID NO: 30:
gggagc(F)aggagagaggu(F)c(F)agau(F)ggu(F)c(F)u(F)
agc(F)c(F)ggaggagu(F)c(F)agu(F)aau(F)c(F)ggu(F)a
gac(F)c(F)u(F)au(F)gc(F)gu(F)gc(F)u(F)agu(F)gu
(F)ga SEQ ID NO: 31:
gggagc(F)aggagagaggu(F)c(F)agau(F)ggaagu(F)ggagu
(F)c(F)agau(F)au(F)agc(F)aau(F)au(F)u(F)au(F)gac
(F)c(F)u(F)au(F)gc(F)gu(F)gc(F)u(F)agu(F)gu(F)ga SEQ ID NO: 32:
gggagc(F)aggagagaggu(F)c(F)agau(F)gggc(F)agc(F)g
gaggau(F)ggc(F)gaagu(F)c(F)au(F)u(F)ggc(F)gc(F)
c(F)u(F)au(F)gc(F)gu(F)gc(F)u(F)ggu(F)ggag SEQ ID NO: 33:
gggagc(F)aggagagaggu(F)c(F)agau(F)ggaggagc(F)c
(F)agu(F)gau(F)c(F)gu(F)u(F)gac(F)c(F)u(F)c(F)aa
u(F)gc(F)ac(F)c(F)u(F)au(F)gc(F)gu(F)gc(F)u(F)ag
u(F)gu(F)ga SEQ ID NO: 34:
gggagc(F)aggagagaggu(F)c(F)agau(F)ggaggagac(F)ag
u(F)gau(F)c(F)gu(F)u(F)gac(F)c(F)c(F)ac(F)c(F)gg
gu(F)c(F)c(F)u(F)au(F)gc(F)gu(F)gc(F)u(F)agu(F)g
u(F)ga SEQ ID NO: 35:
gggagc(F)aggagagaggu(F)c(F)agau(F)ggaggagc(F)ag
u(F)aau(F)c(F)gu(F)u(F)gac(F)u(F)ggu(F)aaac(F)c
(F)c(F)c(F)u(F)au(F)gc(F)gu(F)gc(F)u(F)agu(F)gu
(F)ga SEQ ID NO: 36:
gggagc(F)aggagaggu(F)c(F)agau(F)gu(F)au(F)agc
(F)gaagu(F)c(F)au(F)u(F)gagc(F)gac(F)aaagc(F)c
(F)ggc(F)c(F)u(F)au(F)gc(F)gu(F)gc(F)u(F)agu(F)
gu(F)ga The binding activities for IL-17 of the nucleic acids shown by SEQ ID NOS:1-6 and 29-36 were evaluated by the surface plasmon resonance method. The measurements were taken using BIAcore 2000. The SA chip was used as the sensor chip, which had streptavidin immobilized thereon. Bound thereto was about 600 RU of a 16-nucleotide Poly dT with biotin bound to the 5' end thereof. The ligand nucleic acid had a 16-nucleotide Poly A added to the 3' end thereof, and was immobilized on the SA chip via a bond between dT and A. The amount immobilized was about 800 RU. 20 μL of human IL-17 for analyte, prepared at 0.5 was injected, with the addition of 0.1 mg/mL tRNA to lessen nonspecific adsorption. Solution A was used as a running buffer. As a result of the measurement, it was found that all of the nucleic acids shown by SEQ ID NOS:1-6 and 29-36 bind to IL-17 significantly more than to the negative control 30N. Here, 30N refers to the nucleic acid pool used for the first round of SELEX, comprising a 30-nucleotide random sequence. As an example, a sensorgram showing a status of the binding of the aptamer shown by SEQ ID NO:1 (Apt1) and human IL-17 is shown in FIG. 7. From the above, it was shown that the nucleic acids shown by SEQ ID NOS:1-6 and 29-36 are aptamers that bind to IL-17.

Figure 8:
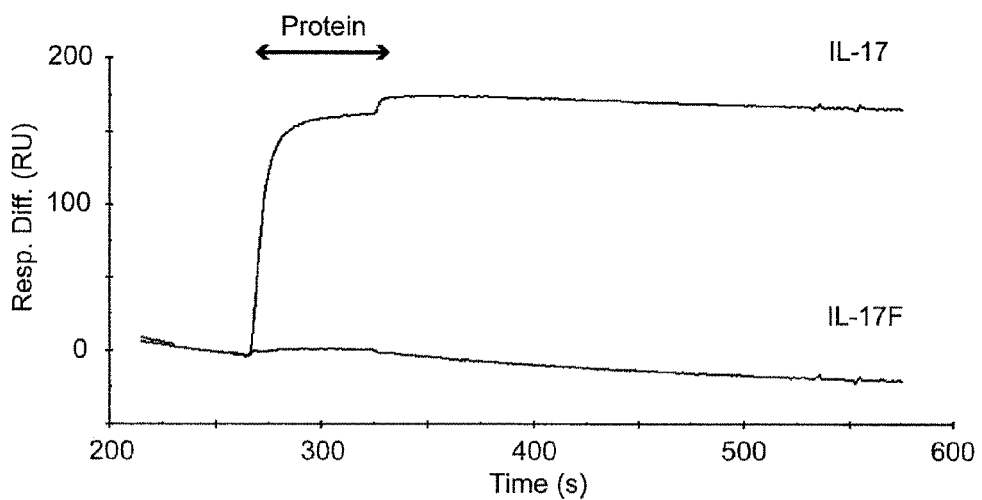
FIG. 8 is a sensorgram showing that the aptamer shown by SEQ ID NO:1 does not bind to human IL-17F.

Whether the IL-17 aptamers shown by SEQ ID NOS:1-6 and 29-36 bind to IL-17F, which belongs to the same family, was determined by the surface plasmon resonance method. The amino acid sequence homology between IL-17 and IL-17F is 50%. The experiment was performed using IL-17F produced by R&D Company (1335-INS/CF), while in a state wherein tRNA was added to lessen nonspecific adsorption as described above. As a result, it was found that none of the aptamers shown by SEQ ID NOS:1-6 and 29-36 binds to IL-17F. As an example, a sensorgram showing that the aptamer shown by SEQ ID NO:1 does not bind to human IL-17F is shown in FIG. 8. From the above, it was found that the aptamers shown by SEQ ID NOS:1-6 and 29-36 bind specifically to IL-17.

Example 2

Shortening of the Aptamers Shown by SEQ ID NOS:1, 2, and 30

Figure 9:
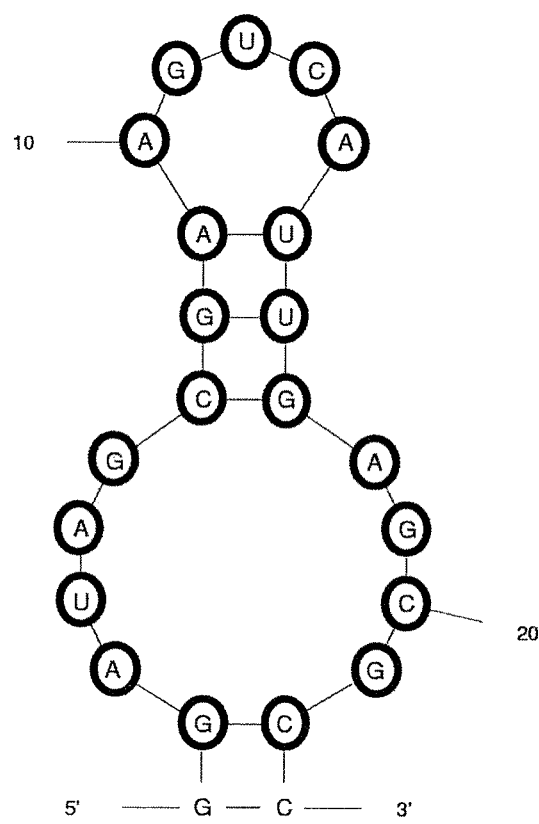
FIG. 9 shows the secondary structure of aptamer shown by SEQ ID NO: 40 predicted by the MFOLD program, wherein the part enclosed in a black circle shows a common sequence.
Figure 10:
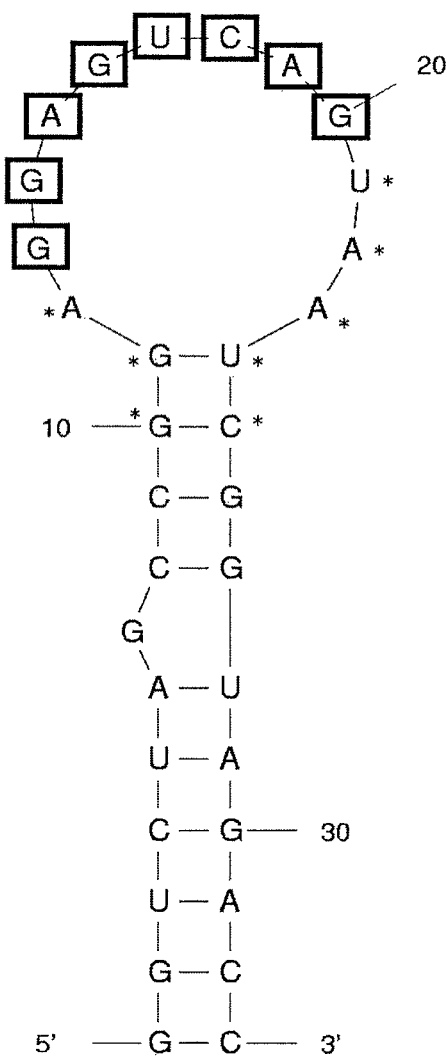
FIG. 10 shows the secondary structure of aptamer shown by SEQ ID NO: 44 predicted by the MFOLD program, wherein the part enclosed in a square and * (asterisk) shows a common sequence.

Shortening of the aptamers shown by SEQ ID NOS:1, 2, and 30 was performed to prepare the nucleic acids shown by SEQ ID NOS:37-44 by chemical synthesis. Whether these nucleic acids possess binding activity for IL-17 was determined by the surface plasmon resonance method in the same manner as Example 1. As a result, all of these nucleic acids were found to possess binding activity for IL-17. The aptamer shown by SEQ ID NO:40 comprises a common sequence contained in the aptamers shown by SEQ ID NOS:1, 2, and 29 (SEQ ID NO:58), and is 23 nucleotides in length. The aptamer shown by SEQ ID NO:44 comprises a common sequence contained in the aptamer shown by SEQ ID NO:30, and is 33 nucleotides in length. The aptamer shown by SEQ ID NO:44 comprises an 8-nucleotide common sequence contained in SEQ ID NOS:6-21, 30, and 31 (SEQ ID NO:59) and a 16-nucleotide common sequence contained in SEQ ID NOS:7, 9, 13, 21 and 30 (SEQ ID NO:60). The secondary structures of the aptamers shown by SEQ ID NOS:40 and 44 as predicted using the MFOLD program are shown in FIGS. 9 and 10, respectively. In FIG. 9, each common sequence is indicated by a black circle. In FIG. 10, the bases of the sequence that is common to SEQ ID NOS:6-21, 30, and 31 are enclosed in squares, and the bases of the sequence that is only common to SEQ ID NOS:7, 9, 13, 21 and 30 are marked with * symbols (asterisks).

Shown below are the respective nucleotide sequences.

SEQ ID NO:37: An aptamer of 54-nucleotide length which is an alteration of the aptamer shown by SEQ ID NO:1 c(F)agau(F)gggc(F)agc(F)agaggau(F)agc(F)gaagu(F)

c(F)au(F)u(F)gagc(F)gc(F)c(F)u(F)au(F)gc(F)gu(F)

gc(F)u(F)agu(F)gu(F)g

SEQ ID NO:38: An aptamer of 40-nucleotide length which is an alteration of the aptamer shown by SEQ ID NO:37 gc(F)agc(F)agaggau(F)agc(F)gaagu(F)c(F)au(F)u(F)

gagc(F)gc(F)c(F)u(F)au(F)gc(F)gu(F)gc(F)

SEQ ID NO:39: An aptamer of 33-nucleotide length which is an alteration of the aptamer shown by SEQ ID NO:38 gc(F)agaggau(F)agc(F)gaagu(F)c(F)au(F)u(F)gagc (F)gc(F)c(F)u(F)au(F)gc(F)

SEQ ID NO:40: An aptamer of 23-nucleotide length which is an alteration of the aptamer shown by SEQ ID NO:39 ggau(F)agc(F)gaagu(F)c(F)au(F)u(F)gagc(F)gc(F)c(F)

SEQ ID NO:41: An aptamer of 27-nucleotide length which is an alteration of the aptamer shown by SEQ ID NO:39 ggggau(F)agc(F)gaagu(F)c(F)au(F)u(F)gagc(F)gc(F)

c(F)c(F)c(F)

SEQ ID NO:42: An aptamer of 41-nucleotide length which is an alteration of the aptamer shown by SEQ ID NO:2 gu(F)gc(F)ac(F)au(F)gggau(F)agc(F)gaagu(F)c(F)a u(F)u(F)gagc(F)gc(F)c(F)u(F)au(F)gc(F)gu(F)gc(F)

SEQ ID NO:43: An aptamer of 52-nucleotide length which is an alteration of the aptamer shown by SEQ ID NO:30 agaggu(F)c(F)agau(F)ggu(F)c(F)u(F)agc(F)c(F)ggag gagu(F)c(F)agu(F)aau(F)c(F)ggu(F)agac(F)c(F)u(F)

au(F)gc(F)gu(F)g

SEQ ID NO:44: An aptamer of 33-nucleotide length which is an alteration of the aptamer shown by SEQ ID NO:30 ggu(F)c(F)u(F)agc(F)c(F)ggaggagu(F)c(F)agu(F)aau (F)c(F)ggu(F)agac(F)c(F)

Example 3

Preparation of Mutants of the Aptamer Shown by SEQ ID NO:40

Mutants were prepared by inducing one mutation to the aptamer shown by SEQ ID NO:40, and their binding activities for IL-17 were evaluated by the surface plasmon resonance method. The sequences and modifications of the mutants are shown below.

SEQ ID NO:45: An aptamer prepared by inducing the mutation (u(F)16:c(F)16) to the aptamer shown by SEQ ID NO:40 ggau(F)agc(F)gaagu(F)c(F)au(F)c(F)gagc(F)gc(F)c(F)

SEQ ID NO:46: An aptamer prepared by inducing the mutation (g21:a21) to the aptamer shown by SEQ ID NO:40 ggau(F)agc(F)gaagu(F)c(F)au(F)u(F)gagc(F)ac(F)c(F)

SEQ ID NO:47: An aptamer prepared by inducing the mutation (c(F)7:a(M)7) to the aptamer shown by SEQ ID NO:40 ggau(F)aga(M)gaagu(F)c(F)au(F)u(F)gagc(F)gc(F)c(F)

SEQ ID NO:48: An aptamer prepared by inducing the mutation (u(F)12:a(M)12) to the aptamer shown by SEQ ID NO:40 ggau(F)agc(F)gaaga(M)c(F)au(F)u(F)gagc(F)gc(F)c(F)

SEQ ID NO:40-2: An aptamer prepared by adding an OMe modification to the a3 of the aptamer shown by SEQ ID NO:40 gga(M)u(F)agc(F)gaagu(F)c(F)au(F)u(F)gagc(F)gc(F)

c(F)

SEQ ID NO:40-3: An aptamer prepared by replacing the c(F)7 of the aptamer shown by SEQ ID NO:40 with c(M)7 ggau(F)agc(M)gaagu(F)c(F)au(F)u(F)gagc(F)gc(F)c(F)

SEQ ID NO:40-4: An aptamer prepared by adding an OMe modification to the g19 of the aptamer shown by SEQ ID NO:40 ggau(F)agc(F)gaagu(F)c(F)au(F)u(F)gag(M)c(F)gc(F)

c(F)

These aptamers all bound to IL-17. This shows that the aptamer shown by SEQ ID NO:40 retains binding activity for IL-17 even after several mutations are introduced or the method of modification is changed.

Example 4

Aptamers that Inhibit the Binding of IL-17 and IL-17 Receptor

Whether the aptamers shown by SEQ ID NOS:1-6 and 29-44 inhibit the binding of IL-17 and IL-17 receptor (IL-17R) was determined using the surface plasmon resonance method.

Figure 11:
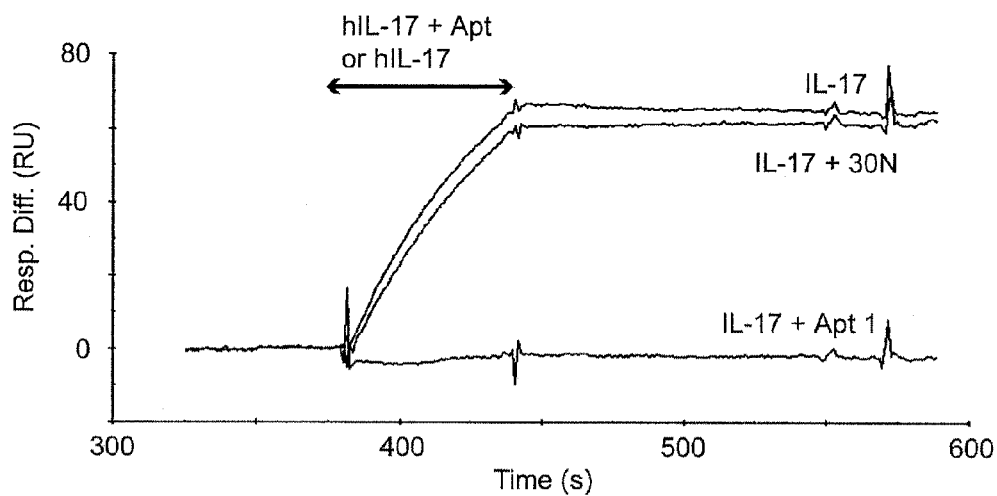
FIG. 11 is a sensorgram showing that the aptamer shown by SEQ ID NO:1 (Apt1) inhibits binding of to human IL-17 and human IL-17R.

As directed in BIAcore Company's protocol, Protein A (21181, PIERCE) was immobilized on a CM5 sensor chip. About 900 RU of human IL-17R-Fc fused with the Fc portion of IgG (177-IR, R&D systems) was immobilized thereon. As the analyte, a mixture of IL-17 (0.11 μM) and each aptamer (0.33 μM) was fed after being allowed to stand for 15 minutes. If the aptamer inhibits the binding of IL-17 and IL-17R, the signal on the sensorgram is not expected to rise; if the aptamer does not inhibit the binding, a tertiary complex will be formed and the signal is expected to rise. Before starting the inhibition experiment, it was confirmed that IL-17 binds to IL-17R. For negative control, a mixture of IL-17 and 30N was used. 30N refers to the nucleic acid pool used for the first round of SELEX, comprising a 30-nucleotide random sequence. As a result of the experiment, it was found that all of the aptamers shown by SEQ ID NOS:1-6 and 29-44 inhibit the binding of IL-17 and IL-17R. Meanwhile, 30N did not exhibit inhibitory activity. As an example, a sensorgram showing that the aptamer shown by SEQ ID NO:1 inhibits the binding of IL-17 and IL-17R is shown in FIG. 11.

From the above, it was shown that the aptamers shown by SEQ ID NOS:1-6 and 29-44 could be used as inhibitors of IL-17.

Example 5

Preparation of Mutants of the Aptamer Shown by SEQ ID NO:44

Mutants were prepared by inducing a mutation to the aptamer shown by SEQ ID NO:44, and whether they inhibited the binding of IL-17 and IL-17R was examined using the surface plasmon resonance method in the same manner as Example 6. The sequences and modifications of the mutants are shown below.

SEQ ID NO:49: An aptamer prepared by inducing a (g7) deletion mutation to the aptamer shown by SEQ ID NO:44 ggu(F)c(F)u(F)ac(F)c(F)ggaggagu(F)c(F)agu(F)aau (F)c(F)ggu(F)agac(F)c(F)

SEQ ID NO:50: An aptamer prepared by inducing a (g14: a14) mutation to the aptamer shown by SEQ ID NO:44 ggu(F)c(F)u(F)agc(F)c(F)ggagaagu(F)c(F)agu(F)aau (F)c(F)ggu(F)agac(F)c(F)

SEQ ID NO:51: An aptamer prepared by inducing a (g20: a20) mutation to the aptamer shown by SEQ ID NO:44 ggu(F)c(F)u(F)agc(F)c(F)ggaggagu(F)c(F)aau(F)

aau(F)c(F)ggu(F)agac(F)c(F)

SEQ ID NO:52: An aptamer prepared by inducing a (g1g2u(F)3c(F)4: G1G2G3G4, g30a31c(F)32c(F)33:C30C31C32C33) mutation to the aptamer shown by SEQ ID NO:44. Here, each capitalized letter indicates a deoxynucleotide.

GGGGu(F)agc(F)c(F)ggaggagu(F)c(F)agu(F)aau(F)c(F)

ggu(F)aCCCC

SEQ ID NO:44-1: An aptamer prepared by inducing a (a19g20:a(M)19g(M)20) mutation to the aptamer shown by SEQ ID NO:44 ggu(F)c(F)u(F)agc(F)c(F)ggaggagu(F)c(F)a(M)g(M)u (F)aau(F)c(F)ggu(F)agac(F)c(F)

SEQ ID NO:44-2: An aptamer prepared by inducing a (a15g16:a(M)15g(M)16) mutation to the aptamer shown by SEQ ID NO:44 ggu(F)c(F)u(F)agc(F)c(F)ggagga(M)g(M)u(F)c(F)agu (F)aau(F)c(F)ggu(F)agac(F)c(F)

SEQ ID NO:53: An aptamer prepared by deleting (g27) and beyond from the aptamer shown by SEQ ID NO:44 ggu(F)c(F)u(F)agc(F)c(F)ggaggagu(F)c(F)agu(F)aau (F)c(F)gg

SEQ ID NO:54: An aptamer prepared by deleting (g1g2u(F) 3) and (a31c(F)32c(F)33) from the aptamer shown by SEQ ID NO:44 c(F)u(F)agc(F)c(F)ggaggagu(F)c(F)agu(F)aau(F)c(F)

ggu(F)ag

SEQ ID NO:44-3: An aptamer prepared by introducing a (a6g7:a(M)6g(M)7) mutation into the aptamer shown by SEQ ID NO:44 ggu(F)c(F)u(F)a(M)g(M)c(F)c(F)ggaggagu(F)c(F)agu
(F)aau(F)c(F)ggu(F)agac(F)c(F)

SEQ ID NO:44-4: An aptamer prepared by introducing a (g10g11:g(M)10g(M)11) mutation into the aptamer shown by SEQ ID NO:44 ggu(F)c(F)u(F)agc(F)c(F)g(M)g(M)aggagu(F)c(F)agu
(F)aau(F)c(F)ggu(F)agac(F)c(F)

SEQ ID NO:44-5: An aptamer prepared by introducing a (a12g13:a(M)12g(M)13) mutation into the aptamer shown by SEQ ID NO:44 ggu(F)c(F)u(F)agc(F)c(F)gga(M)g(M)gagu(F)c(F)agu
(F)aau(F)c(F)ggu(F)agac(F)c(F)

SEQ ID NO:44-6: An aptamer prepared by introducing a (g14a15:g(M)14a(M)15) mutation into the aptamer shown by SEQ ID NO:44 ggu(F)c(F)u(F)agc(F)c(F)ggagg(M)a(M)gu(F)c(F)agu
(F)aau(F)c(F)ggu(F)agac(F)c(F)

SEQ ID NO:44-7: An aptamer prepared by introducing a (a22a23:a(M)22a(M)23) mutation into the aptamer shown by SEQ ID NO:44 ggu(F)c(F)u(F)agc(F)c(F)ggagga(M)gu(F)c(F)agu(F)a
(M)a(M)u(F)c(F)ggu(F)agac(F)c(F)

SEQ ID NO:44-8: An aptamer prepared by adding PEG40 (SUNBRIGHT GL2-400GS2, produced by NOF Corporation Company) to the 5' end of the aptamer shown by SEQ ID NO:44, and adding idT (inverted dT) to the 3' end thereof.

PEG40-ggu(F)c(F)u(F)agc(F)c(F)ggaggagu(F)c(F)agu
(F)aau(F)c(F)ggu(F)agac(F)c(F)-idT These aptamers all inhibited the binding of IL-17 and IL-17 receptor (IL-17R). This shows that the aptamer shown by SEQ ID NO:44 retains inhibitory activity against the binding of IL-17 and IL-17 receptor (IL-17R) even after several mutations are introduced or the method of modification is changed.

Example 6

Aptamers Inhibit IL-17 Signaling in Cultured Cells

Figure 12:
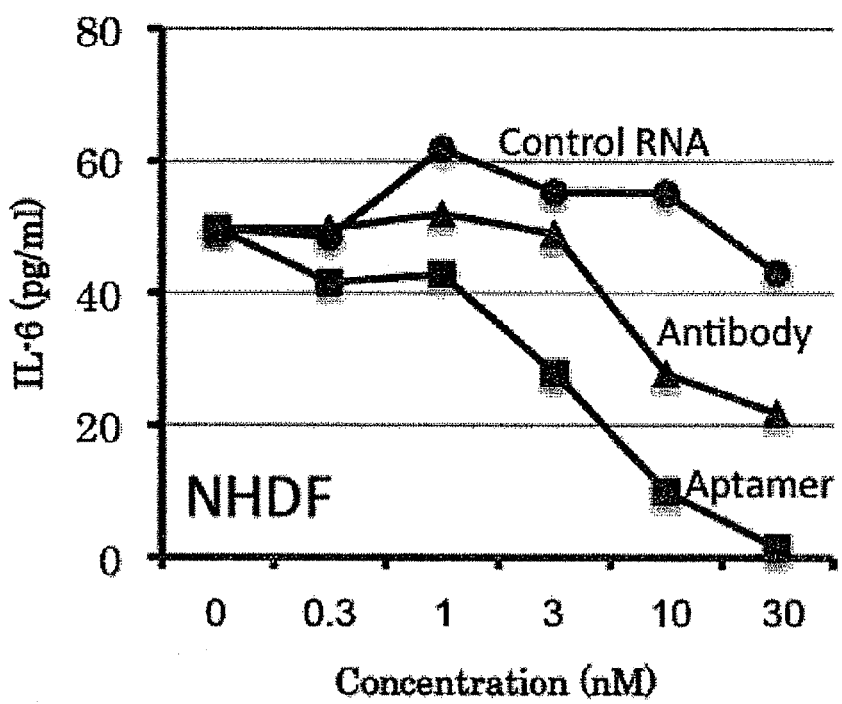
FIG. 12 shows that the aptamer shown by SEQ ID NO:44 possesses inhibitory activity against IL-17 signaling. Black circles show the results for a control DNA, black triangles show the results for an anti-IL-17 neutralizing antibody, and black squares show the results for an aptamer, respectively.

Whether the aptamer shown by SEQ ID NO:44 is capable of inhibiting the cell stimulation by IL-17 was determined using normal human dermal fibroblasts (NHDF, Sanko Junyaku). When stimulated with IL-17, NHDF cells produce interleukin 6 (IL-6) extracellularly. When the NHDF cells were stimulated with human IL-17 (produced by Peprotech Company) (40 ng/ml), an aptamer (the aptamer shown by SEQ ID NO:44) was added to the medium, and the IL-6 produced 24 hours later was measured by an enzyme-linked immunosorbent assay (ELISA) method (Endogen Human IL-6 ELISA Kit: Thermo scientific). Results for the inhibition of IL-6 production are shown in FIG. 12. As a result of the measurement, it was confirmed that when the aptamer was added, IL-6 production was suppressed dose-dependently. A higher inhibitory effect than that of an anti-IL-17 neutralizing antibody (MAB421, produced by R&D Systems) was obtained. Meanwhile, the control RNA did not exhibit inhibitory activity. Here, the control RNA refers to the nucleic acid pool used in the first round of SELEX, comprising a 30-nucleotide random sequence. These findings showed that the aptamer of the present invention possesses high inhibitory activity against IL-17 signaling in surviving cells as well.

Example 7

Experiment of Pathogenesis Suppression in Mouse Model of Aptamer-Induced EAE (Experimental Autoimmune Encephalomyelitis)

The influence on aptamer on pathogenesis was analyzed using the mouse EAE model, which is known as a mouse model of human multiple sclerosis. 300 µg of the myelin oligodendrocyte glycoprotein peptide 35-55 ($MOG_{35-55}$) (MEVGWYRSPFSRVVHLYRNGK (SEQ ID NO: 61)) was emulsified with Freund's incomplete adjuvant containing 500 µg of tubercle bacillus (Mycobacterium tuberculosis), and this emulsion was subcutaneously administered to the axillary and lumbar regions of wild C57BL/6 mice (female, 8-weeks of age) to sensitize the animals. Furthermore, immediately after the sensitization and 48 hours later, 200 ng of pertussis toxin was dissolved in 200 µL of PBS and administered to the tail vein to induce EAE. Thereafter, clinical symptoms were evaluated everyday using the criteria shown below.

For a group of wild mice (n=10) and groups of mice receiving the aptamer shown by SEQ ID NO:44-8 (n=10 for each of 1 mg/kg, 3 mg/kg, and 10 mg/kg), clinical scores were recorded every day, and clinical symptoms were evaluated. Clinical score values were rated as 0: no symptoms, 0.5: the tail drooping half, 1: the tail drooping fully, 2: disturbance of gait, 3: paralysis of one limb, 4: paralysis of both hind limbs, 5: forelimb hemiplegia, 6: forelimb paralysis/death; the scores for all animals were recorded until day 25 after administration of $MOG_{35-55}$.

The aptamer shown by SEQ ID NO:44-8 was dissolved in physiological saline, and this was administered 13 times in total at intervals of two days from the day of administration of $MOG_{35-55}$. For a control group, the same quantity of physiological saline was administered in the same way.

Figure 13:
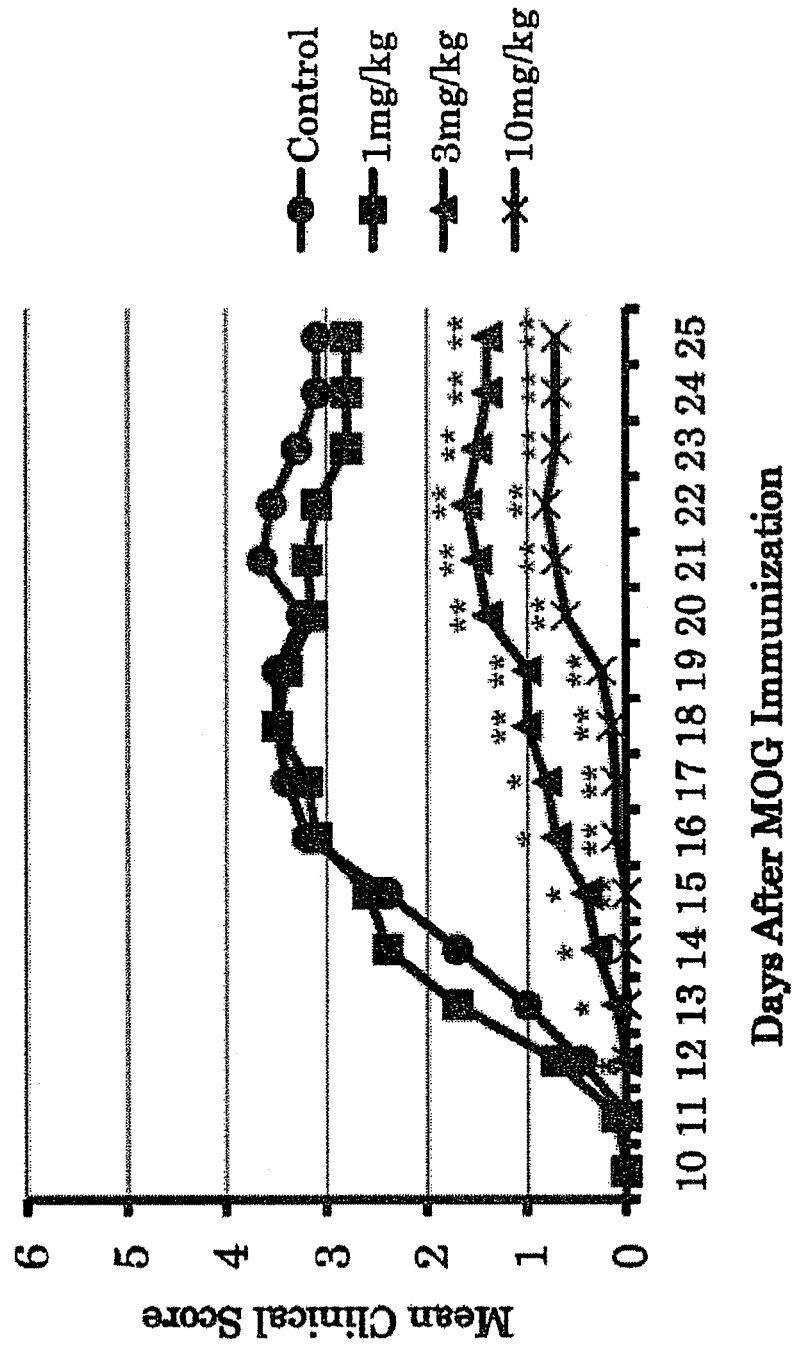
FIG. 13 shows the results of an experiment of pathogenesis suppression by an aptamer in a mouse model of EAE. Black circles show the results for a control group, black squares show the results for a group receiving the aptamer at 1 mg/kg, black triangles show the results for a group receiving the aptamer at 3 mg/kg, and Xs show the results for a group receiving the aptamer at 10 mg/kg, respectively. Each * (asterisk) indicates P<0.05, and each ** indicates P<0.01.

The time course of the evaluation of clinical symptoms is shown in FIG. 13. Compared with the control group, no significant difference was seen in the group receiving the aptamer shown by SEQ ID NO:44-8 at 1 mg/kg. Meanwhile, in the groups receiving the aptamer shown by SEQ ID NO:44-8 at 3 mg/kg and 10 mg/kg, mitigation of the clinical symptoms was seen with a statistically significant difference. Statistically significant differences were analyzed using the Mann-Whitney U-test and Dunnett's method. In the figure, statistically significant differences (*: $P<0.05$, **: $P<0.01$) are shown. The results above strongly suggest that aptamers against IL-17 may be utilized as therapeutic drugs for autoimmune diseases such as multiple sclerosis.

INDUSTRIAL APPLICABILITY

The aptamer or the complex of the present invention can be useful as a pharmaceutical or reagent such as a diagnostic reagent for inflammatory diseases, and diseases such as cancer, allergy, infectious disease and the like. The aptamer or the complex of the present invention can also be useful in purifying and concentrating IL-17, labeling of IL-17, and detecting and quantifying IL-17.

This application is based on a patent application No. 2008-183233 filed in Japan, the contents of which are incorporated in full herein by this reference.

The invention claimed is:

1. An aptamer that binds to IL-17A and inhibits the binding of IL-17A and IL-17 receptor, comprising the nucleotide sequence of SEQ ID NOs: 58, 59 or 60, wherein the length of the aptamer is not more than 100 nucleotides.

2. The aptamer according to claim 1, wherein the aptamer does not inhibit the binding of IL-17F and IL-17 receptor.

3. The aptamer according to claim 1, wherein a pyrimidine nucleotide contained in the aptamer is modified.

4. The aptamer according to claim 1, which is either (a) or (b) below:
   (a) an aptamer comprising a nucleotide sequence selected from the group consisting of SEQ ID NOs: 1, 2, 6-21, 29-31, 37-44, 49, and 52-54 (with the provision that uracil may be thymine), wherein each ribose 2'-hydroxyl group of the nucleotides contained in the aptamer is independently unsubstituted or substituted by an atom or group selected from the group consisting of hydrogen atom, methoxy group and fluorine atom, or
   (b) an aptamer comprising a nucleotide sequence selected from the group consisting of SEQ ID NOs: 1, 2, 6-21, 29-31, 37-44, 49, and 52-54 (with the provision that the uracil may be thymine), wherein one to three nucleotides are substituted, deleted, inserted or added, wherein each ribose 2'-hydroxyl group of the nucleotides contained in the aptamer is independently unsubstituted or substituted by an atom or group selected from the group consisting of hydrogen atom, methoxy group and fluorine atom.

5. The aptamer according to claim 4, comprising the sequence of SEQ ID NO: 40 or 44.

6. The aptamer according to claim 1, wherein a nucleotide contained in the aptamer is modified.

7. A complex comprising the aptamer according to claim 1 and a functional substance.

8. The complex according to claim 7, wherein the functional substance is a substance for labeling, an enzyme, a drug delivery vehicle or a drug.

9. A pharmaceutical composition comprising the aptamer according to claim 1 and a pharmaceutically acceptable carrier.

10. A method of inhibiting IL-17A-stimulated inflammation in a subject comprising administering to the subject an effective amount of the aptamer according to claim 1, thereby inhibiting IL-17A-stimulated inflammation in the subject.

11. A method of detecting IL-17A, comprising (a) contacting a test sample with the aptamer according to claim 1 to allow IL-17A in the test sample to bind to the aptamer, and (b) detecting the IL-17A bound to the aptamer.

12. A method of purifying IL-17A, comprising (a) contacting a sample comprising IL-17A with the aptamer according to claim 1 to allow IL-17A in the sample to bind to the aptamer, and (b) separating the IL-17A bound to the aptamer from the sample.

13. An aptamer that binds to IL-17A and inhibits the binding of IL-17A and IL-17 receptor, which is either (a) or (b) below:
   (a) an aptamer comprising a nucleotide sequence selected from the group consisting of SEQ ID NOs: 3-5, 22-28, 32-36, 45-48, 50, and 51 (with the provision that uracil may be thymine), wherein each ribose 2'hydroxyl group of the nucleotides contained in the aptamer is independently unsubstituted or substituted by an atom or group selected from the group consisting of hydrogen atom, methoxy group, and fluorine atom, or
   (b) an aptamer comprising a nucleotide sequence selected from the group consisting of SEQ ID NOs: 3-5, 22-28, 32-36, 45-48, 50, and 51 (with the provision that uracil may be thymine), wherein one to three nucleotides are substituted, deleted, inserted or added, and wherein each ribose 2'hydroxyl group of the nucleotides contained in the aptamer is independently unsubstituted or substituted by an atom or group selected from the group consisting of hydrogen atom, methoxy group, and fluorine atom.

\* \* \* \* \*

UNITED STATES PATENT AND TRADEMARK OFFICE
CERTIFICATE OF CORRECTION

PATENT NO.        : 8,440,801 B2
APPLICATION NO.   : 13/003240
DATED             : May 14, 2013
INVENTOR(S)       : Nakamura et al.

It is certified that error appears in the above-identified patent and that said Letters Patent is hereby corrected as shown below:

IN THE SPECIFICATION

Column 3, lines 38-39, "that the uracil may be thymine" should read "that uracil may be thymine"

Column 3, lines 50-51, "that the uracil may be thymine" should read "that uracil may be thymine"

Column 7, lines 58-59, "that the uracil may be thymine" should read "that uracil may be thymine"

Column 7, lines 61-62, "that the uracil may be thymine), wherein one to several nucleotides" should read "that uracil may be thymine), wherein one or several nucleotides"

Column 12, line 58, "periarthritis nodosa (PN)" should read "periarteritis nodosa (PN)"

Column 14, line 14, "tetrahydroflufuryl oleate" should read "tetrahydrofurfuryl oleate"

Column 15, lines 58-59, "for example, a potassium salt (e.g., NaCl, KCl)," should read "for example, a sodium salt (e.g., NaCl), a potassium salt (e.g., KCl),"

IN THE CLAIMS

Claim 4, column 51, lines 32-33, "that the uracil may be thymine" should read "that uracil may be thymine"

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,440,801 B2  
APPLICATION NO. : 13/003240  
DATED : May 14, 2013  
INVENTOR(S) : Yoshikazu Nakamura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 130 days.

Signed and Sealed this
Sixteenth Day of December, 2014

Michelle K. Lee
*Deputy Director of the United States Patent and Trademark Office*

SEQUENCE LISTING

```
<160> NUMBER OF SEQ ID NOS: 61

<210> SEQ ID NO 1
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 1
gggagcagga gagaggucag augggcagca gaggauagcg aagucauuga gcgccuaugc    60
gugcuagugu ga                                                        72

<210> SEQ ID NO 2
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 2
gggagcagga gagaggucag auggugcaca ugggauagcg aagucauuga gcgccuaugc    60
gugcuagugu ga                                                        72

<210> SEQ ID NO 3
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 3
gggagcagga gagaggucag auguguaagg ucggaaguca ugaacggccc ggaccuaugc    60
gugcuagugu ga                                                        72

<210> SEQ ID NO 4
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 4
gggagcagga gagaggucag augcuauagc gaagucauug agcgagacau aggccuaugc    60
gugcuagugu ga                                                        72

<210> SEQ ID NO 5
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17
```

```
<400> SEQUENCE: 5
gggagcagga gagaggucag augagcgcca uagggugagag aagccauuga ucaccuaugc      60
gugcuagugu ga                                                           72

<210> SEQ ID NO 6
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 6
gggagcagga gagaggucag auggugaugc auaggagugg agucagauau agcccuaugc      60
gugcuagugu ga                                                           72

<210> SEQ ID NO 7
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 7
gggagcagga gagaggucag auguguacgu uaggagggag gagucaguaa ucgccuaugc      60
gugcuagugu ga                                                           72

<210> SEQ ID NO 8
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 8
gggagcagga gagaggucag auggaggagu cagcaaucgu uggccuucug cgaccuaugc      60
gugcuagugu ga                                                           72

<210> SEQ ID NO 9
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 9
gggagcagga gagaggucag auggaggagu caguaaucgu uggcccugcu ucaccuaugc      60
gugcuagugu ga                                                           72

<210> SEQ ID NO 10
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 10
gggagcagga gagaggucag auggaggagu cagugaucag ugaccucuug uggccuaugc      60
gugcuagugu ga                                                           72
```

```
<210> SEQ ID NO 11
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 11
gggagcagga gagaggucag augguggagu cagugagcgu ugaccggcaa ucaccuaugc        60
gugcuagugu ga                                                            72

<210> SEQ ID NO 12
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 12
gggagcagga gagaggucag auggaggagu cagugaucgu ugccggacuu gccccuaugc        60
gugcuagugu ga                                                            72

<210> SEQ ID NO 13
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 13
gggagcagga gagaggucag auggaggagu caguaaucgu ugaaccggag cauccuaugc        60
gugcuagugu ga                                                            72

<210> SEQ ID NO 14
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 14
gggagcagga gagaggucag augaugacag gagucagaua uaugcacauu ugaccuaugc        60
gugcuagugu ga                                                            72

<210> SEQ ID NO 15
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 15
gggagcagga gagaggucag augguuaggu ggagucaggg aaaaaaccgu uugccuaugc        60
gugcuagugu ga                                                            72

<210> SEQ ID NO 16
<211> LENGTH: 72
<212> TYPE: RNA
<213> ORGANISM: Artificial Sequence
```

```
<220> FEATURE:
<223> OTHER INFORMATION: Synthetic nucleic acid having binding activity
      against interleukin-17

<400> SEQUENCE: 16
gggagcagga gagaggucag auguagagug gagucagaua uagccuacaa gucccuaugc        60
gugcuagugu ga                                                           72

<210> SEQ ID NO 17
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 17
gggagcagga gagaggucag auguaauagg ggagucagau auaccaacga agaccuaugc        60
gugcuagugu ga                                                           72

<210> SEQ ID NO 18
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 18
gggagcagga gagaggucag auguaauagg ggagucagau auaccaacga agaccuaugc        60
gugcuagugu ga                                                           72

<210> SEQ ID NO 19
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 19
gggagcagga gagaggucag augcgaucgu acgcgggggg ggagucagau auaccuaugc        60
gugcuagugu ga                                                           72

<210> SEQ ID NO 20
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 20
gggagcagga gagaggucag augugauagu acgcggaagg ggagucagau auaccuaugc        60
gugcuagugu ga                                                           72

<210> SEQ ID NO 21
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17
```

```
<400> SEQUENCE: 21
gggagcagga gagaggucag augcaaggag gagucaguaa ucgugacauu ggcccuaugc 60
gugcuagugu ga 72

<210> SEQ ID NO 22
<211> LENGTH: 72
<212> TYPE: RNA
<213> ORGANISM: Artificial Sequence
<220> FEATURE:
<223> OTHER INFORMATION: Synthetic nucleic acid having binding activity against interleukin-17

<400> SEQUENCE: 22
gggagcagga gagaggucag augcuaugcc gcacaaacac guaugagugc ucaccuaugc 60
gugcuagugu ga 72

<210> SEQ ID NO 23
<211> LENGTH: 72
<212> TYPE: DNA
<213> ORGANISM: Artificial Sequence
<220> FEATURE:
<223> OTHER INFORMATION: Synthetic nucleic acid having binding activity against interleukin-17

<400> SEQUENCE: 23
gggagcagga gagaggucag augguuacuu cccaaaaguc auaaaugggg uuaccuaugc 60
gugcuagugu ga 72
```

```
<210> SEQ ID NO 24
<211> LENGTH: 72
<212> TYPE: RNA
<213> ORGANISM: Artificial Sequence
<220> FEATURE:
<223> OTHER INFORMATION: Synthetic nucleic acid having binding activity against interleukin-17

<400> SEQUENCE: 24
gggagcagga gagaggucag auggaggaga caguaaucgu ugaccgcuuc gugccuaugc 60
gugcuagugu ga 72

<210> SEQ ID NO 25
<211> LENGTH: 72
<212> TYPE: RNA
<213> ORGANISM: Artificial Sequence
<220> FEATURE:
<223> OTHER INFORMATION: Synthetic nucleic acid having binding activity against interleukin-17

<400> SEQUENCE: 25
gggagcagga gagaggucag augugauagc gaaggcauug agcgcacauu aaaccuaugc 60
gugcuagugu ga 72

<210> SEQ ID NO 26
<211> LENGTH: 71
<212> TYPE: RNA
<213> ORGANISM: Artificial Sequence
<220> FEATURE:
<223> OTHER INFORMATION: Synthetic nucleic acid having binding activity against interleukin-17

<400> SEQUENCE: 26
gggagcagga gagaggucag augggcagca gaggaugcga agucauugag cgccuaugcg 60
ugcuagugug a 71
```

```
<210> SEQ ID NO 27
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 27
gggagcagga gagaggucag augccuggua ggcguagaga agucauugau cagccuaugc      60
gugcuagugu ga                                                         72

<210> SEQ ID NO 28
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 28
gggagcagga gagaggucag auguuauaaa agcuuaagug cugucaacuu cuaccuaugc      60
gugcuagugu ga                                                         72

<210> SEQ ID NO 29
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 29
gggagcagga gagaggucag augcgauagc gaagucauug agcgcguguc caaccuaugc      60
gugcuagugu ga                                                         72

<210> SEQ ID NO 30
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 30
gggagcagga gagaggucag auggucuagc cggaggaguc aguaaucggu agaccuaugc      60
gugcuagugu ga                                                         72

<210> SEQ ID NO 31
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 31
gggagcagga gagaggucag auggaagugg agucagauau agcaauauua ugaccuaugc      60
gugcuagugu ga                                                         72

<210> SEQ ID NO 32
<211> LENGTH: 72
<212> TYPE: RNA
<213> ORGANISM: Artificial Sequence
```

```
<220> FEATURE:
<223> OTHER INFORMATION: Synthetic nucleic acid having binding activity
      against interleukin-17

<400> SEQUENCE: 32
gggagcagga gagaggucag augggcagcg gaggauggcg aagucauugg gcgccuaugc    60
gugcuggugg ag                                                        72

<210> SEQ ID NO 33
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 33
gggagcagga gagaggucag auggaggagc cagugaucgu ugaccucaau gcaccuaugc    60
gugcuagugu ga                                                        72

<210> SEQ ID NO 34
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 34
gggagcagga gagaggucag auggaggaga cagugaucgu ugacccaccg gguccuaugc    60
gugcuagugu ga                                                        72

<210> SEQ ID NO 35
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 35
gggagcagga gagaggucag auggaggagg caguaaucgu ugacugguaa accccuaugc    60
gugcuagugu ga                                                        72

<210> SEQ ID NO 36
<211> LENGTH: 72
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 36
gggagcagga gagaggucag auguauagcg aagucauuga gcgacaaagc cggccuaugc    60
gugcuagugu ga                                                        72

<210> SEQ ID NO 37
<211> LENGTH: 54
<212> TYPE: RNA
<213> ORGANISM: Artificial Sequence
<220> FEATURE:
<223> OTHER INFORMATION: Synthetic nucleic acid having binding activity
      against interleukin-17
```

```
<400> SEQUENCE: 37
cagaugggca gcagaggaua gcgaagucau ugagcgccua ugcgugcuag ugug        54

<210> SEQ ID NO 38
<211> LENGTH: 40
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 38
gcagcagagg auagcgaagu cauugagcgc cuaugcgugc                        40

<210> SEQ ID NO 39
<211> LENGTH: 33
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 39
gcagaggaua gcgaagucau ugagcgccua ugc                               33

<210> SEQ ID NO 40
<211> LENGTH: 23
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 40
ggauagcgaa gucauugagc gcc                                          23

<210> SEQ ID NO 41
<211> LENGTH: 27
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 41
ggggauagcg aagucauuga gcgcccc                                      27

<210> SEQ ID NO 42
<211> LENGTH: 41
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 42
gugcacaugg gauagcgaag ucauugagcg ccuaugcgug c                      41

<210> SEQ ID NO 43
<211> LENGTH: 52
<212> TYPE: RNA
<213> ORGANISM: Artificial Sequence
<220> FEATURE:
<223> OTHER INFORMATION: Synthetic nucleic acid having binding activity
      against interleukin-17
```

```
<400> SEQUENCE: 43
agaggucaga uggucuagcc ggaggaguca guaaucggua gaccuaugcg ug        52

<210> SEQ ID NO 44
<211> LENGTH: 33
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 44
ggucuagccg gaggagucag uaaucgguag acc                             33

<210> SEQ ID NO 45
<211> LENGTH: 23
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 45
ggauagcgaa gucaucgagc gcc                                        23

<210> SEQ ID NO 46
<211> LENGTH: 23
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 46
ggauagcgaa gucauugagc acc                                        23

<210> SEQ ID NO 47
<211> LENGTH: 23
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 47
ggauagagaa gucauugagc gcc                                        23

<210> SEQ ID NO 48
<211> LENGTH: 23
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 48
ggauagcgaa gacauugagc gcc                                        23

<210> SEQ ID NO 49
<211> LENGTH: 32
<212> TYPE: RNA
<213> ORGANISM: Artificial Sequence
<220> FEATURE:
<223> OTHER INFORMATION: Synthetic nucleic acid having binding activity
      against interleukin-17
```

-continued

```
<400> SEQUENCE: 49
ggucuaccgg aggagucagu aaucgguaga cc                                      32

<210> SEQ ID NO 50
<211> LENGTH: 33
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 50
ggucuagccg gagaagucag uaaucgguag acc                                     33

<210> SEQ ID NO 51
<211> LENGTH: 33
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 51
ggucuagccg gaggagucaa uaaucgguag acc                                     33

<210> SEQ ID NO 52
<211> LENGTH: 33
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 52
gggguagccg gaggagucag uaaucgguac ccc                                     33

<210> SEQ ID NO 53
<211> LENGTH: 27
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 53
ggucuagccg gaggagucag uaaucgg                                            27

<210> SEQ ID NO 54
<211> LENGTH: 27
<212> TYPE: RNA
<213> ORGANISM: Artificial Sequence
<220> FEATURE:
<223> OTHER INFORMATION: Synthetic nucleic acid having binding activity
      against interleukin-17

<400> SEQUENCE: 54
cuagccggag gagucaguaa ucgguag                                            27

<210> SEQ ID NO 55
<211> LENGTH: 72
<212> TYPE: DNA
<213> ORGANISM: Artificial Sequence
<220> FEATURE:
<223> OTHER INFORMATION: Synthetic template DNA
<220> FEATURE:
<221> NAME/KEY: misc_feature
<222> LOCATION: (20)..(49)
<223> OTHER INFORMATION: n is a, c, g, or t
```

```
<400> SEQUENCE: 55
tcacactagc acgcataggn nnnnnnnnnn nnnnnnnnnn nnnnnnnnnc atctgacctc      60
tctcctgctc cc                                                         72

<210> SEQ ID NO 56
<211> LENGTH: 40
<212> TYPE: DNA
<213> ORGANISM: Artificial Sequence
<220> FEATURE:
<223> OTHER INFORMATION: Synthetic primer

<400> SEQUENCE: 56
taatacgact cactataggg agcaggagag aggtcagatg                           40

<210> SEQ ID NO 57
<211> LENGTH: 19
<212> TYPE: DNA
<213> ORGANISM: Artificial Sequence
<220> FEATURE:
<223> OTHER INFORMATION: Synthetic primer

<400> SEQUENCE: 57
tcacactagc acgcatagg                                                  19

<210> SEQ ID NO 58
<211> LENGTH: 21
<212> TYPE: RNA
<213> ORGANISM: Artificial Sequence
<220> FEATURE:
<223> OTHER INFORMATION: Synthetic consensus sequence

<400> SEQUENCE: 58
gauagcgaag ucauugagcg c                                               21

<210> SEQ ID NO 59
<211> LENGTH: 8
<212> TYPE: RNA
<213> ORGANISM: Artificial Sequence
<220> FEATURE:
<223> OTHER INFORMATION: Synthetic consensus sequence

<400> SEQUENCE: 59 ggagucag                                                              8

<210> SEQ ID NO 60
<211> LENGTH: 16
<212> TYPE: RNA
<213> ORGANISM: Artificial Sequence
<220> FEATURE:
<223> OTHER INFORMATION: Synthetic consensus sequence

<400> SEQUENCE: 60
ggaggaguca guaauc                                                     16

<210> SEQ ID NO 61
<211> LENGTH: 21
<212> TYPE: PRT
<213> ORGANISM: Artificial Sequence
<220> FEATURE:
<223> OTHER INFORMATION: Synthetic Sequence
```

-continued

```
<400> SEQUENCE: 61

Met Glu Val Gly Trp Tyr Arg Ser Pro Phe Ser Arg Val Val His Leu
1               5                   10                  15

Tyr Arg Asn Gly Lys
            20
```